(12) United States Patent
Butters et al.

(10) Patent No.: US 8,729,099 B2
(45) Date of Patent: May 20, 2014

(54) PHARMACEUTICALLY ACTIVE PIPERIDINE DERIVATIVES

(75) Inventors: Terence D. Butters, Oxford (GB); Raymond A. Dwek, Oxford (GB); George W. J. Fleet, Oxford (GB); Michael Glen Orchard, Abingdon (GB); Frances Mary Platt, Oxford (GB)

(73) Assignee: Actelion Pharmaceuticals Ltd., Allschwil (CH)

( * ) Notice: Subject to any disclaimer, the term of this patent is extended or adjusted under 35 U.S.C. 154(b) by 545 days.

(21) Appl. No.: 11/196,153

(22) Filed: Aug. 3, 2005

(65) Prior Publication Data
US 2006/0074107 A1  Apr. 6, 2006

Related U.S. Application Data

(60) Division of application No. 10/618,165, filed on Jul. 11, 2003, now abandoned, which is a continuation-in-part of application No. PCT/GB02/00106, filed on Jan. 11, 2002.

(51) Int. Cl.
*A61K 31/445* (2006.01)
*C07D 211/22* (2006.01)

(52) U.S. Cl.
USPC .......................................... 514/315; 546/246

(58) Field of Classification Search
USPC .......................................... 514/315; 546/246
See application file for complete search history.

(56) References Cited

U.S. PATENT DOCUMENTS

| | | | |
|---|---|---|---|
| 4,407,809 A | 10/1983 | Junge et al. |
| 4,639,436 A | 1/1987 | Junge et al. |
| 4,639,463 A | 1/1987 | Rosner et al. |
| 5,003,072 A | 3/1991 | Partis et al. |
| 5,051,407 A | 9/1991 | Boshagen et al. |
| 5,276,120 A | 1/1994 | Wong et al. |
| 5,798,366 A | 8/1998 | Platt et al. |
| 6,046,214 A | 4/2000 | Kristiansen et al. |
| 6,225,325 B1 | 5/2001 | Jacob |
| 6,426,198 B1 | 7/2002 | Carstea et al. |
| 6,495,570 B2 | 12/2002 | Jacob et al. |
| 6,683,076 B2 | 1/2004 | Walkley et al. |
| 7,256,005 B2 | 8/2007 | Zitzmann et al. |
| 7,985,760 B2 | 7/2011 | Ali |
| 7,994,198 B2 | 8/2011 | Ali |
| 8,022,219 B2 | 9/2011 | Orchard et al. |
| 8,071,780 B2 | 12/2011 | Orchard |
| 2001/0044453 A1 | 11/2001 | Jacob et al. |
| 2004/0019082 A1 | 1/2004 | van der Spoel et al. |
| 2006/0058349 A1 | 3/2006 | Ali et al. |
| 2006/0111400 A1 | 5/2006 | Ali et al. |
| 2007/0112028 A1 | 5/2007 | Orchard et al. |
| 2007/0259918 A1 | 11/2007 | Orchard |
| 2008/0234324 A1 | 9/2008 | Orchard |

FOREIGN PATENT DOCUMENTS

| | | |
|---|---|---|
| DE | 3024901 A | 1/1982 |
| EP | 0491041 | 6/1992 |
| EP | 0 536 402 A | 4/1993 |
| EP | 0536402 | 4/1993 |
| EP | 0698012 | 1/1997 |
| EP | 698 102 B1 | 3/2006 |
| JP | A-02/306962 | 12/1990 |
| JP | H02-306962 | 12/1990 |
| JP | 3-24057 | 2/1991 |
| WO | WO 92/00277 | 1/1992 |
| WO | WO 94/26714 | 11/1994 |
| WO | WO 98/02161 | 1/1998 |
| WO | WO 98/30219 | 7/1998 |
| WO | WO 99/24401 | 5/1999 |
| WO | WO 00/33843 | 6/2000 |
| WO | WO 00/56334 | 9/2000 |
| WO | WO 00/62780 | 10/2000 |
| WO | WO 01/10429 A2 | 2/2001 |
| WO | WO 02/055498 | 7/2002 |
| WO | WO 2004/007453 | 1/2004 |
| WO | WO 2004/007454 | 1/2004 |
| WO | WO 2004/111001 | 12/2004 |
| WO | WO 2004/111002 | 12/2004 |
| WO | WO 2005/068426 | 7/2005 |

OTHER PUBLICATIONS

Frances Platt et al N-Butyldeoxynojirimycin is a novel inhibitor of Glycolipid Biosynthesis 1994, vol. 269, Issue 11, pp. 8362-8365.*
Akira Abe et al Induction of glucosylceramide synthase by synthase inhibitors and ceramide 1996 pp. 333-341.*
Herman S. Overkleeft et al Generation of specific Deoxynojirimycin-type inhibitors of the Non-lysosomal glucosylceramidase 1998.*
Lin and Lu et al Role of Pharmacokinetics and Metabolism in Discovery and Development , 1997.*
Drug Chirality Hutt and O'Grady 1996.*
Racemates Versus Enantiomers in Drug Development Testa et al. 1990.*
Clinical and Pharmacology and Therapeutics Drayer et al 1986.*

(Continued)

*Primary Examiner* — Rita Desai
(74) *Attorney, Agent, or Firm* — Hoxie & Associates LLC

(57) ABSTRACT

Compounds of formula (I):

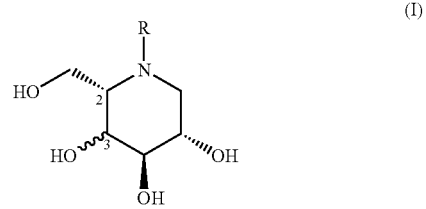

wherein R represents various substituent groups, are useful as inhibitors of glucosylceramide synthase.

3 Claims, No Drawings

(56) References Cited

OTHER PUBLICATIONS

Abe, A., et al., "Reduction of globotriaosylceramide in fabry disease mice by substrate deprivation," *J. of Clin. Invest.*, Jun. 2000, 105(11), 1563-1571.

Asano, N., et al., Novel α-L-fucosidase inhibitors from the bark of *Angylocalyx pynaertii* (leguminosae), *Eur. J. Biochem.*, 2001, 268, 35-41.

Asano, K., "New entry for asymmetric deoxyazasugar synthesis: syntheses of deoxymannojirimycin, deoxyaltrojirimycin and deoxygalactostatin," *Chem. Commun.*, 1999, 41-42.

Barili, P.L., et al., "Double reductive amination of L-*arabino*-Hexos-5-uloses: a diastereoselective approach to 1-deoxy-D-galactostatin derivatives (#)(°)," *Tetrahedron*, 1997, 53(9), 3407-3416.

Baxter, E.W., et al., "Expeditious synthesis of azasugars by the double reductive amination of dicarbonyl sugars," *J. Org. Chem.*, 1994, 59, 3175-3185.

Bernotas, R.C., et al., "Efficient preparation of enantiomerically pure cyclic aminoalditols total synthesis of 1-deoxynojirimycin and 1-deoxymannojirimycin," *Tetrahedron Letts.*, 1985, 26(9), 1123-1126.

Biochemical Genetics, A Laboratory Manual, Oxford University Press.

Chen, C.-S., et al., "Abnormal transport along the lysosomal pathway in mucolipidosis, type IV disease," *Proc. Natl. Acad. Sci. USA*, May 1998, 95, 6373-6378.

Cox, T., et al., "Novel oral treatment of gaucher's disease with N-butyldeoxynojirimycin (OGT 918) to decrease substrate biosynthesis," *The Lancet*, Apr. 29, 2000, 355, 1481-1485.

Fouace, S., et al., "Lipophilic prodrugs of 1-deoxynojirimycin derivatives," *Tetrahedron Letts.*, 2000, 41, 7313-7315.

Fowler, P.A., et al., "Synthesis and activity towards yeast α-glucosidase of 1,5-dideoxy-1,5 imino-L-iditol (1-deoxy-L-idonojirimycin)," *Carbohydrate Res.*, 1993, 246, 377-381.

Godskesen, M., et al., "Deoxyiminoalditols from aldonolactones—V. preparation of the four stereoisomers of 1,5-dideoxy-1,5-iminopentitols. Evaluation of these iminopentitols and three 1,5-dideoxy-1,5-iminoheptitols as glycosidase inhibitors," *Bioorganic & Medicinal Chem.*, 1996, 4(11), 1857-1865.

Goodman, L.A., et al., "Ectopic dendrites occur only on cortical pyramidal cells containing elevated GM2 ganglioside in α-mannosidosis," *Proc. Natl. Acad. Sci. USA*, Dec. 1991, 88, 11330-11334.

Grandel, R., et al., "A short synthesis of azasugars via aldol reaction of chelated amino acid ester enolates," *Tetrahedron Letts.*, 1997, 38(46), 8009-8012.

Greene, et al., Protective Groups in Organic Chemistry, 2$^{nd}$ Ed., Wiley-Interscience, NY, 1991.

Hügel, H.M., et al., "Stereoselective electrophilic cyclizations of δ-aminoalkenes derived from carbohydrates: synthesis of polyhydroxypiperidines," *Aust. J. Chem.*, 1998, 51, 1149-1155.

Ikota, N., et al., "Improved synthesis of 1-deoxynojirimycin and facile synthesis of its stereoisomers from (S)-pyroglutamic acid derivative," *Heterocycles*, 1997, 46, 637-643.

Jeyakumar, M., et al., "Delayed symptom onset and increased life expectancy in sandhoff disease mice treated with N-butyldeoxynojirimycin," *Proc. Natl. Acad. Sci. USA*, May 1999, 96, 6388-6393.

Kajimoto, T., et al., "Palladium-mediated stereocontrolled reductive amination of azido sugars prepared from enzymatic adol condensation: a general approach to the synthesis of deoxy aza sugars," *J. Am. Chem. Soc.*, 1991 113, 6678-6680.

Kazmaier, U., et al., "A short synthesis of polyhydroxylated piperidines by adol reaction of chelated amino acid ester enolates," *Eur. J. Org. Chem.*, 1998, 1833-1840.

Lee, B.W., et al., "A short and efficient synthesis of 2R,3R,4R-3,4-dihydroxyproline, 1,4-dideoxy-1,4-imino-L-xylitol, 2R,3R,4R,5S-3,4,5-trihydroxypipecolic acid, and 1,5-dideoxy-1,5-imino-L-iditol," *Synthesis*, 2000, 9, 1305-1309.

Le Merrer, Y., et al., "Synthesis of azasugars as potent inhibitors of glycosidases," *Bioorganic & Medicinal Chem.*, 1997, 5(3), 519-533.

Liotta, L.J., et al., "A new class of endoglycosidase inhibitors. Studies on endocellulases," *J. Am. Chem. Soc.*, 1989, III, 783-785.

Liu, Y.-Y., et al., "Uncoupling ceramide glycosylation by transfection of glucosylceramide synthase antisense reverses adriamycin resistance," *J. of Biol. Chem.*, Mar. 10, 2000, 275(10), 7138-7143.

Lundt, I., et al., "Deoxyiminoalditols from aldonolactones; IV: preparation of 1,5-dideoxy-1,5-iminoheptitols with L-*glycero*-D-*manno*, D-glycero-L-*gulo* and L-*glycero*-D-*altro* configuration," *Synthesis*, Jul. 1995, 787-794.

Mehta, G., et al., "A norbornyl route to azasugars: a new synthesis of deoxynojirimycin analogues," *Tetrahedron Letts*, 2000, 41, 5741-5745.

Mellor, H.R., "High-performance cation-exchange chromatography and pulsed amperometric detection for the separation, detection, and quantitation of N-alkylated imino sugars in biological samples," *Analytical Biochemistry*, XP-001055984, 2000, 284, 136-142.

Paulsen, H., et al., "Über monosaccharide mit stickstoffhaltigem siebenring," *Chem. Ber.*, 1967, 100, 512-520 (German language); Chemical Abstracts #3208 "Thymine nucleosides of 3-deoxy-d-xylo-hexose," p. 3207.

Paulsen, H., et al., "Synthese and reaktionen von keto-piperidinosen," *Chem. Ber.*, 1967, 100, 802-815 (English Abstract).

Platt, F.M., et al., "N-butyldeoxygalactonojirimycin inhibits glycolipid biosynthesis but does not affect N-linked oligosaccharide processing," *J. of Biol. Chem.*, Oct. 28, 1994, 269(43), 27108-27114.

Platt, F.M., et al., "Prevention of lysosomal storage in tay-sachs mice treated with N-butyldeoxynojirimycin," *Science*, Apr. 18, 1997, 276, 428-431.

Poitout, et al., "Synthesis of azasugars.$^1$ Part 1$^2$ Isomerization of polyhydroxylated piperidines," *Tetrahedron Letts.*, 1996, 37(10), 1609-1612.

Rao, V.S., et al., "Regioselective eliminations in reactions of carbohydrate derivatives with superoxide, or with borohydride in 2-propanol," *Can. J. Chem.*, 1981, 59, 333-338.

Reitz, A.B., et al., "Pyrrolidine and piperidine aminosugars from dicarbonyl sugars in one step. Concise synthesis of 1-deoxyojirimycin," *Tetrahedron Letts.*, 1990, 31(47), 6777-6780.

Schaller, C., et al., "Total synthesis of (+)- and (−)-1-deoxynojirimycin (1,5-dideoxy-1,5-imino-D- and L-glucitol) and of (+)- and (−)-1-deoxyidonojirimycin (1,5-dideoxy-1,5-imino-D- and L-iditol) via furoisoxazoline-3-aldehydes," *Carbohydrate Res.*, 1998, 314, 25-35.

Simons K., et al., "Functional rafts in cell membranes," *Nature*, Jun. 5, 1997, 387, 569-572.

Subramanian, T., et al., "Synthesis of oxazolidinyl azacycles via ring-closing olefin metathesis: a practical entry to the synthesis of deoxy-azasugars and hydroxypyrrolizidines," *Tetrahedron Letts.*, 2001, 42, 4079-4082.

Uriel, C., et al., "A short and efficient synthesis of 1,5-dideoxy-1,5-imino-D-galactitol (1-deoxy-D-galactostatin) and 1,5-dideoxy-1,5-imino-L-altritol (1-deoxy-L-altrostatin) from D-galactose," *Synlett*, 1999, 5, 593-595.

Xu, Y.-M., et al., "A new approach to 1-deoxy-azasugars: asymmetric synthesis of 1-deoxymannojirimycin and 1-deoxyaltronojirimycin," *J. Chem. Sco. Perkin Trans.*, 1997, 1, 741-746.

Alessandri et al., Angiogenic and antiostatis microenvironment in tumors, Acta. Oncol. 36, 383-387 (1997).

Alter, GMI ganglioside for acute ischemic stroke—trial design issues, Ann.Ny Acad. Sci., 845, 391-401 (1998).

Berg et al., Herbicidal composition containing piperidine derivatives, CAPLUS, 96:117597 (1982).

Boeshagen et al., Use of hydroxymethyl-3,4,5-trihydroxypiperidines as antiviral agents, CAPLUS, 113:126581 (1990).

Bramer et al., Biologic activity of 5'-deoxy-5-fluorouridine by rectal administration, Pharmaceutical Res., 6(4), 318-322 (1989).

Chatterjee et al., Role of lactosylceramide and MAP kinase in the proliferation of proximal tubular cells in human polycystic kidney disease, J. of Lipid, Res., 37, 1334-1344 (1996).

Choo-Smith et al., Acceleration of amyloidfibril formation by specific binding of Aβ-(1-40) peptide to ganglioside-containing membrane vesicles, J. of Biol. Chem., 272(37), 22987-22990 (1997).

De Man et al., Bacterial adherence as a virulence factor in urinary tract infection, APMIS, 98, 1053-1060 (1990).

(56) References Cited

OTHER PUBLICATIONS

Ezure et al., Preparation of 1-deoxygalactostatin derivatives as β-galactosidase inhibitors, CAPLUS, 116:236093 (1992).
Geisler, Clinical trials of pharmacotherapy for spinal cord injury, Ann. NY Acad. Sci., 845, 375-381 (1998).
Greene, Protective groups in organic synthesis, Wiley-Interscience Publication, pp. cover, 10, 11, 29 (1982).
Handa et al., Analysis of glycolipid-dependent cell adhesion based on carbohydrate-carbohydrate interaction, Methods in Ensymol., 312, 447-458, (2000).
Hansson et al., A novel approach to the study of glycolipid receptors for viruses, FEBS Lett., 170(1), 15-18 (1984).
Jaranowska et al., Platelet-activating factor production by human fetal microglia, Mol. & Chem. Neuropathol., 24, 95-106 (1995).
Jimenez-Lucho et al., *Cryptococcus neoformans, Candida albicans*, and other fungi bind specifically to the glycosphingolipid lactosylceramide (Galβ1-4Glcβ1-1Cer), a possible adhesion receptor for yeasts, Infect. & Immun., 58(7), 2085-2090 (1990).
Kurihara et al., Preparation of N-substituted 1-deoxynojirimycins as tumor metastasis inhibitors, CAPLUS, 114:185939 (1991).
Kato et al., Biological properties of D- and L-1 deoxyazasugars, J.Med.Chem, 48, pp. 2036-2044 (2005).
Lavie et al., Agents that reverse multidrug resistance, tamoxifen, verapamil, and cyclosporine A, block glycosphingolipid metabolism by inhibiting ceramide glycosylation in human cancer cells, J. of Biol. Chem., 272(3), 1682-1687 (1997).
Le Merrer et al., Synthesis of azasugars as potent inhibitors of glycosidases, 5(3), 519-533 (1997).
Li et al., Cellular gangliosides promote growth factor-induced proliferation of fibroblasts, J. of Biol. Chem., 275(44), 34213-34223 (2000).
Lingwood et al., Analysis of interactions between glycospingolipids and microbial toxins, Methods in Enzymol., 312, 459-473 (2000).
Lucci et al., Glycosylceramide: a marker for multiple-drug resistant cancers, Anticancer Res., 18, 475-480 (1998).
Mc Kallip et al., Tumor gangliosides inhibit the tumor-specific immune response, J. Immunol., 163, 3718-3726 (1999).
Memon et al., Regulation of glycosphingolipid metabolism in liver during the acute phase response, J. of Biol. Chem., 274(28), 19707-19713 (1999).
Memon et al., Regulation of sphingolipid and glycosphingolipid metabolism in extrahepatic tissues by entotoxin, J. of Lipid. Res., 42, 452-459 (2001).
Merzak et al., Gangliosides modulate proliferation, migration, and invasiveness of human brain tumor cells in vitro, Mol. & Chem. Nueuropathology, 24, 121-135 (1995).
Nicholson et al., Preferential killing of multidrug-resistant KB cells by inhibitors of glucosylceramide synthase, Br. J. Cancer, 81(3), 423-430 (1999).
Overkleeft et al., Generation of specific deoxynojirimycin-type inhibitors of the non-lysosomal glucosylceramidase, J. of Biol. Chem. 23(43), 27108-27114 (1994).
Prokazova et al., Gangliosides and atherosclerosis, Lipids, 29, 1-5 (1994).
Ryan et al., Changes in membrane gangliosides: differentiation of human and murine monocytic cells, Yale J. of Biol. Med., 58, 125-131 (1985).
Schneider, GM1 ganglioside in the treatment of Parkinson's Disease, Ann. NY Acad. Sci., 845, 363-373 (1998).
Svensson et al., Carbohydrate receptor depletion as an antimicrobial strategy for prevention of urinary tract infection, J. of Infect. Dis., 183 (Suppl.1), S70-S73 (2001).
Tyle, Iontophoretic devices for drug delivery, Pharm. Res., 3, 318-326 (1986).
Van Den Broek et al., Chemical modification of aza sugars, inhibitors of N-glycoprotein-processing glycosidases and of HIV-I infection, CAPLUS, 119:96007 (1993).
Van Der Spoel et al., Proc. Natl. Acac. Sci. USA, 99(26), 17173-17178 (2002).

Yanagisawa et al., GM1 ganglioside-bound amyloid β-protein (Aβ): a possible form of preamyloid in Alzheimer's Disease, Nat. Med., 1(10), 1062-1066 (1995).
Yohe et al., Ganglioside alternations in stimulated murine macrophages, Biochimica et Biophys. Acta, 818, 81-86 (1985).
Yohe et al., Ganglioside expression in macrophages from endotoxin responder and nonresponder mice, J. of Immunol., 137, 3921-3927 (1986).
Yohe et al., The presence of sialidase-sensitive sialosylgangliotetraosyl ceramide ($G_{M1b}$ in stimulated murine macrophages, J. of Immunol, 146, 1900-1908 (1991).
Zador et al., A role for glycosphingolipid accumulation in the renal hypertrophy of steptozotocin-induced diabetes mellitus, J. Clin. Invest., 91, 797-803 (1993).
Cruz, J.C., et al., Fate of Endogenously Synthesized Cholesterol in Niemann-Pick Type C1 Cells, The Journal of Biological Chemistry, 2000, Issue of Dec. 29, vol. 275, No. 52, pp. 41309-41316.
Liu, Y. et al., Alleviation of neuronal ganglioside storage does not improve the clinical course of the Niemann-Pick C disease mouse, Human Molecular Genetics, 2000, vol. 9., No. 7, pp. 1087-1092.
Platt, F.M. et al., New Therapeutic Prospects for the Glycosphingolipid Lysosomal Storage Diseases, Biochemical Pharmacology, 1998, vol. 56, pp. 421-430.
Zervas, M. et al., Critical role for glycosphingolipids in Niemann-Pick disease type C, Current Biology, 2001, 11, pp. 1283-1287.
Silva, et al., Advances in Prodrug Design, Mini-Reviews in Medicinal Chemistry, 2005, vol. 5, pp. 893-914.
Wu, W. et al., Synthesis and Biological Activity of a Gemcitabine Phosphoramidate Prodrug, J. Med. Chem., 2007, vol. 50(15); pp. 3743-3746.
Yildiz, Y. et al., Mutation of β-glucosidase 2 causes glycolipid storage disease and impaired male fertility. The Journal of Clinical Investigation. 2006, vol. 116, No. 11, pp. 2985-2994.
Butters et al., Therapeutic applications of imino sugars in lysosomal storage disorders, Current Topics in Medicinal Chemistry, 3, 561-574 (2003).
Platt et al; "Extensive Glycosphingolipid Depletion in the Liver and Lymphoid Organs of Mice Treated with N-Butyldeoxynojirimycin"; The Journal of Biological Chemistry; vol. 272, No. 31; pp. 19365-19372, 1997.
Butters et al; "Molecular Requirements of Imino Sugars for the Selective Control of N-linked Glycosylation and Glycosphingolipid Biosynthesis"; Tetrahedron: Asymmetry; 11 (2000) 113-124.
Office Actions from U.S. Patent No. 7,985,760 dated Jun. 4, 2009, Dec. 11, 2008 and Jul. 29, 2008.
Office Actions from U.S. Patent No. 7,994,198 dated Jun. 3, 2009, Dec. 18, 2008 and Jul. 28, 2008.
Office Actions from U.S. Patent No. 8,022,219 dated Dec. 7, 2010, Apr. 6, 2010 and Dec. 30, 2009.
Office Actions from U.S. Patent No. 8,071,780 dated Feb. 3, 2011, Jul. 30, 2010, Apr. 9, 2010, and Dec. 30, 2009.
Office Action from U.S. Publication No. 2008/0234324 dated Mar. 2, 2009.
Butters et al; "Inhibition of Glycosphingolipid Biosynthesis: Application to Lysosomal Storage Disorders"; Chem. Rev. 2000; 100; 4683-4696.
Weiss et al., "Inhibition of Melanoma Tumor Growth by a Novel Inhibitor of Glucosylceramide Synthase"; Cancer Research 63; 3654-3658; Jul. 1, 2003.
Abe, A. et al., "Agents for the Treatment of Glycosphingolipid Storage Disorders", Current Drug Metabolism, (2001), vol. 2, pp. 331-338.
Tifft, C. J., et al., "Stemming the Tide: Glycosphingolipid Synthesis Inhibitors as Therapy for Storage Diseases", Glycobiology, vol. 10, No. 12, pp. 1249-1258, (2000).

* cited by examiner

PHARMACEUTICALLY ACTIVE PIPERIDINE DERIVATIVES

CROSS REFERENCE TO RELATED APPLICATIONS

This application is a divisional of U.S. application Ser. No. 10/618,165, filed Jul. 11, 2003 now abandoned, which is a continuation-in-part of International Application No. PCT/GB02/00106, filed Jan. 11, 2002, which claims the benefit of Great Britain Application No. 0100889.5, filed Jan. 12, 2001, each of which is incorporated herein by reference in its entirety.

The present invention relates to novel piperidine derivatives useful as inhibitors of glucosylceramide synthase (GCS; UDP-glucose:ceramide glycosyltransferase UDP-glucose:N-acylsphingosine D-glucosyltransferase, EC 2.4.1.80), methods for their preparation and their use in medicine, specifically in the treatment and prevention of disease states mediated by GCS. The compounds find use in the treatment of glycolipid storage diseases, diseases associated with glycolipid accumulation, cancers in which glycolipid synthesis is abnormal, infectious diseases caused by organisms which use cell surface glycolipid as receptors, infectious diseases in which synthesis of glucosylceramide is essential or important, diseases in which excessive glycolipid synthesis occurs, neuronal disorders and neuronal injury. Their synthesis is also described, as are pharmaceutical formulations comprising the compounds and methods of treatment using the compounds.

GCS is an intracellular enzyme that catalyzes the assembly of uridine diphosphate-glucose and ceramide into the glycolipid, glucosylceramide. GCS's role in biology is currently the subject of intense basic and applied science interest. For example, many investigators are exploring the role of GCS in regulating ceramide levels since this molecule can induce apoptotic cell death (J. Biol. Chem., Mar. 10, 2000, 275(10), 7138-43). Similarly, there is active research into the role of GCS in maintaining cholesterol/glycolipid 'rafts,' cell-surface membrane domains of specialized permeability and functionality that appear to be involved in a variety of signal transduction events (Nature, Jun. 5, 1997, 387(6633), 569-72).

GCS also is a target for treating certain human diseases. Glucosylceramide and structurally related glycolipids are stored in the lysosomes of patients with genetic diseases which result from a mutation in one of the essential glycolipid-degrading enzymes (e.g., Gaucher, Tay Sachs, Sandhoffs, GM1 gangliosidosis and Fabry diseases). Glycolipid storage also occurs as a secondary effect in some tissues (e.g., neuronal tissue) with genetic storage diseases such as Niemann-Pick C disease, mucopolysaccharidoses, mucolipidosis type IV (Proc. Natl. Acad. Sci. USA, May 26, 1998, 95(11), 6373-8) and α-mannosidosis (Proc. Natl. Acad. Sci. USA, Dec. 15, 1991, 88(24), 11330-4). It has been reasoned that GCS inhibitors may be applied to reduce the rate of glycolipid synthesis in diseased cells so that there is less glycolipid present to be stored, a treatment approach termed substrate deprivation. Studies have demonstrated that GCS inhibitors can in fact be used to reduce the glycolipid accumulation seen in cell and animal models of glycolipid storage (Proc. Natl. Acad. Sci. USA, May 25, 1999, 96(11), 6388-93; Science, Apr. 18, 1997, 276(5311), 428-31; J. Clin. Invest., June 2000, 105(11), 1563-71). Furthermore, a recent clinical trial report has shown that GCS inhibitors such as N-butyldeoxynojirimycin (NB-DNJ) are useful in treating human patients with Gaucher disease (Lancet, Apr. 29, 2000, 355 (9214), 1481-5). The use of the imino sugar NB-DNJ as a GCS inhibitor is disclosed in EP-A-0698012. EP-A-0536402 and EP-A-0698012 disclose that N-alkyl derivatives of deoxygalactonojirimycin, e.g. N-butyldeoxygalactonojirimycin (NB-DGJ), may also be of use in the treatment of glycolipid storage disorders. EP-A-0698012 also discloses that the corresponding N-butyl derivatives of mannose (NB-DMJ), fucose (NB-DFJ) and N-acetylglucosamine (NB-NAG) do not act as inhibitors of glycolipid biosynthesis.

The use of GCS inhibitors in the treatment of human malignancies has been proposed. Tumours can synthesize abnormal quantities of glycolipids and/or glycolipids not present in the normal tissue. In addition glycolipids or gangliosides in particular are shed by tumour cells and released into the extracellular space and the bloodstream. Both tumour shed and cell surface bound tumour gangliosides can influence tumour host cell interactions such as cell-cell contacts or adhesion (Methods Enzymol., 2000, 312, 447-58), cell motility (Mol. Chem. Neuropathol., 1995 Feb.-Apr., 24(2-3), 121-35), growth factor signalling events (J. Biol. Chem., 2000 Nov. 3, 275(44), 34213-23), tumour stimulated angiogenesis (Acta. Oncol., 1997, 36(4), 383-7) and tumour specific immune responses (J. Immunol., 1999 Oct. 1, 163(7), 3718-26). All these events can affect tumour development and progression. Glycolipids, glucosylceramide in particular, are known to accumulate in multidrug resistant (MDR) tumour cells (Anticancer Res., 1998 Jan.-Feb., 18(1B), 475-80) and in vitro treatment of these cells with GCS inhibitors can reverse the MDR phenotype (J. Biol. Chem., 1997, Jan. 17, 272(3), 1682-7; Br. J. Cancer, 1999, Oct., 81(3), 423-30).

Cell surface glycolipids also have roles in infectious disease, serving as receptors for the binding of pathogenic bacteria (APMIS, 1990, Dec., 98(12), 1053-60, Review), fungi (Infect. Immun., 1990 Jul., 58(7), 2085-90) and viruses (FEBS Lett., 1984 May 7, 170(1), 15-8). In addition, glycolipids on the surface of cells are bound by bacterial toxins (Methods Enzymol., 2000, 312, 459-73) for instance the B subunit of cholera toxin (ganglioside GM1) and verocytotoxin (globotriaosylceramide GB3) (J. Infect. Dis., 2001, suppl. 70-73, 183).

The use of GCS inhibitors may also be appropriate in a number of other clinical indications which are associated with abnormalities in glycolipid synthesis. Atherosclerotic lesions of human aorta have a higher ganglioside content than unaffected regions of the aorta and serum ganglioside concentrations in atherosclerotic patients are higher than in normal individuals (Lipids, 1994, 29(1), 1-5). Tissue derived from the kidneys of patients with polycystic kidney disease contains high levels of both glucosylceramide and lactosylceramide (J. Lipid. Res., 1996, Jun., 37(6), 1334-44). Renal hypertrophy in an animal model of diabetes is associated with increases in glycolipid synthesis, (J. Clin. Invest., 1993, Mar., 91(3), 797-803).

Glycolipid metabolism also plays a critical role in other neuronal disorders, such as Alzheimer's disease and epilepsy. For instance, Niemann-Pick C (NPC) patient neurons present with fibrillar tangles reminiscent of the morphology seen in Alzheimer's disease.

Interestingly, GM1 ganglioside binding by amyloid beta-protein induces conformational changes that support its formation of fibrous polymers, and the fibrillar deposition of this protein is an early event in Alzheimer's disease (Yanagisawa et al, (1995), Nat. Med. 1, 1062-6; Choo-Smith et al, (1997), Biol. Chem., 272, 22987-90). Thus, decreasing GM1 synthesis with agents such as NB-DNJ could inhibit the fibre formation seen in Alzheimer's disease.

In contrast, preliminary clinical trials have shown that neurodegenerative processes seen with Parkinson's disease, stroke and spinal cord injuries seem to improve by treating patients with GM1 ganglioside (Alter, (1998), Ann. NY Acad. Sci. 845, 391-4011; Schneider, (1998), Ann. NY. Acad. Sci., 845, 363-73; Geisler, (1998), Ann. NY. Acad. Sci., 845, 374-81). It is possible that co-administering glucosylceramide synthesis inhibitors would provide the clinician greater control over this treatment course. Inhibitors like NB-DNJ would limit patient-specific inconsistencies by blocking their neuronal glycolipid synthesis. In addition, inhibiting glucosylceramide synthesis would limit the metabolism of administered glycolipids into other, perhaps unproductive, forms. Thus, the ability to modulate glucosylceramide synthesis with inhibitors such as NB-DNJ may be useful is treatment of a wide variety of neuronal disorders.

It has also been shown that imino sugars can reversibly induce male sterility and can therefore be used as male contraceptives.

The compound 3,4,5-piperidinetriol, 1-butyl-2-(hydroxymethyl)-, (2S,3R,4R,5S) is disclosed in Anal. Biochem., 2000, 284 (1), 136-142 as an analytical comparator, no pharmaceutical utility is disclosed or suggested for this compound.

WO 01/10429 (published after the priority date of this application) discloses the compound N-nonyl-altrostatin (3,4,5-piperidinetriol, 1-nonyl-2-(hydroxymethyl)-, (2S,3S, 4R,5S)) and it's use in the treatment of viral infections.

Tet. Lett., 1990, 31(47) 6777-80 discloses the compound 3,4,5-piperidinetriol, 1-phenylmethyl-2-(hydroxymethyl)-, (2S,3R,4R,5S) as a minor by-product in the synthesis of 3,4,5-piperidinetriol, 1-phenylmethyl-2-(hydroxymethyl)-, (2R,3R,4R,5S), no pharmaceutical utility is disclosed or suggested for this compound. The compounds piperidine, 1-phenylmethyl-3,4,5-tris(phenylmethoxy)-2-[(phenylmethoxy)-methyl], (2S,3R,4R,5S) and piperidine,l-phenylmethyl-3,4, 5-tris(acetyloxy)-2-[(acetyloxy)-methyl], (2S,3R,4R,5S) are also disclosed as by-products obtained in the synthesis of the corresponding (2R,3R,4R,5S) compounds.

Tetrahedron, 1997, 53(9), 3407-16 discloses the compounds piperidine, 1-phenylmethyl-3,4,5-di(acetyloxy)-5-(phenylmethoxy)-2-[(phenylmethoxy)-methyl], (2S,3S,4R, 5S) and piperidine,l-methyl-3,4,5-di(acetyloxy)-5-(phenylmethoxy)-2- [(phenylmethoxy)-methyl], (2S,3S,4R, 5S) as a by-products obtained in the synthesis of the corresponding (2R,3S,4R,5S) compounds.

Bioorganic and Medicinal Chemistry, 1996, 4(11), 1857-65 discloses the compound piperidine, 1-phenylmethyl-3,4-di(phenylmethoxy)-5-(benzoyloxy)-2-[(phenylmethoxy)-methyl], (2S,3R,4R,5S) as an intermediate in the synthesis of 3,4,5-piperidinetriol, 2-(hydroxymethyl)-, (2S,3R,4R,5S).

Given the importance of GCS in a wide spectrum of basic and applied science interests, it is essential that new tools that provide a means for modulating this enzyme's function be developed. Towards this end, we have synthesized a number of novel compounds that are useful in inhibiting GCS's catalytic activity.

According to the invention there is provided a compound of formula (I) or a pharmaceutically acceptable salt or prodrug thereof:

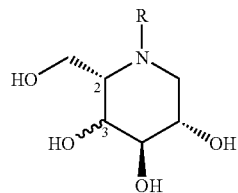

wherein
R is $C_{1-16}$ straight or branched-chain alkyl, optionally substituted by $C_{3-7}$cycloalkyl, and optionally interrupted by —O— the oxygen being separated from the ring nitrogen by at least two carbon atoms, or $C_{1-10}$ alkylaryl where aryl is phenyl, pyridyl, thienyl or furyl wherein phenyl is optionally substituted by one or more substituents selected from F, Cl, Br, $CF_3$, $OCF_3$, $OR^1$, and $C_{1-6}$ straight or branched-chain alkyl; and
$R^1$ is hydrogen, or $C_{1-6}$ straight or branched-chain alkyl;
provided that the compound is not:
a) 3,4,5-piperidinetriol, 1-butyl-2-(hydroxymethyl)-, (2S, 3R,4R,5S);
b) 3,4,5-piperidinetriol, 1-phenylmethyl-2-(hydroxymethyl)-, (2S,3R,4R,5S);
c) 3,4,5-piperidinetriol, 1-nonyl-2-(hydroxymethyl)-, (2S, 3S,4R,5S);
d) 3,4,5-piperidinetriol, 1-dodecyl-2-(hydroxymethyl)-, (2S,3R,4R,5S); or
e) 3,4,5-piperidinetriol, 1-(1-phenyl)ethyl-2-(hydroxymethyl)-, (2S,3R,4R,5S).

The hydroxyl group at position 3 may be fixed in either the R or the S configuration. The hydroxyl group at position 3 is preferably in the R configuration, i.e. the compound of formula (I) has the stereochemistry (2S,3R,4R,5S).

R is preferably $C_{1-16}$ straight or branched-chain alkyl or $C_{1-10}$ alkylphenyl wherein phenyl is optionally substituted by one or more substituents selected from F, Cl, Br, $CF_3$, $OCF_3$, $OR^1$, and $C_{1-16}$ straight or branched-chain alkyl. R is more preferably $C_{1-16}$ straight or branched-chain alkyl. Even more preferably R is $C_{3-10}$ straight chain alkyl, especially $C_{4-7}$ straight chain alkyl.

The compounds for use in the methods of the invention preferably have a molecular weight of less than 800, more preferably less than 600.

Specific compounds of the invention that may be mentioned include the following:
3,4,5-piperidinetriol, 1-propyl-2-(hydroxymethyl)-, (2S, 3R,4R,5S);
3,4,5-piperidinetriol, 1-pentyl-2-(hydroxymethyl)-, (2S, 3R,4R,5S);
3,4,5-piperidinetriol, 1-heptyl-2-(hydroxymethyl)-, (2S, 3R,4R,5S);
3,4,5-piperidinetriol, 1-butyl-2-(hydroxymethyl)-, (2S,3S, 4R,5S);
3,4,5-piperidinetriol, 1-nonyl-2-(hydroxymethyl)-, (2S, 3R,4R,5S);
3,4,5-piperidinetriol, 1-(1-ethyl)propyl-2-(hydroxymethyl)-, (2S,3R,4R,5S);
3,4,5-piperidinetriol, 1-(3-methyl)butyl-2-(hydroxymethyl)-, (2S,3R,4R,5S); 3,4,5-piperidinetriol, 1-(2-phenyl)ethyl-2-(hydroxymethyl)-, (2S,3R,4R,5S);
3,4,5-piperidinetriol, 1-(3-phenyl)propyl-2-(hydroxymethyl)-, (2S,3R,4R,5S); 3,4,5-piperidinetriol, 1-(1-ethyl)hexyl-2-(hydroxymethyl)-, (2S,3R,4R,5S);

3,4,5-piperidinetriol, 1-(2-ethyl)butyl-2-(hydroxymethyl)-, (2S,3R,4R,5S); 3,4,5-piperidinetriol, 1-[(2R)-(2-methyl-2-phenyl)ethyl]-2-(hydroxymethyl)-, (2S,3R,4R,5S);

3,4,5-piperidinetriol, 1-[(2S)-(2-methyl-2-phenyl)ethyl]-2-(hydroxymethyl)-, (2S,3R,4R,5S);

and pharmaceutically acceptable salts and prodrugs thereof.

A particularly preferred compound is 3,4,5-piperidinetriol, 1-pentyl-2-(hydroxymethyl)-, (2S,3R,4R,5S) and pharmaceutically acceptable salts thereof.

A specific group of compounds according to the invention which may be mentioned are those of formula (Ia) or a pharmaceutically acceptable salt thereof:

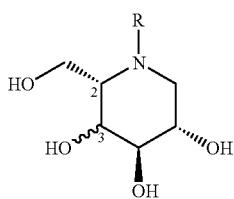

(Ia)

wherein

R is $C_{1-16}$ straight or branched-chain alkyl, or $C_{1-10}$ alkylaryl where aryl is phenyl, pyridyl, thienyl or furyl wherein phenyl is optionally substituted by one or more substituents selected from F, Cl, Br, $CF_3$, $OCF_3$, $OR^1$, $C_{1-6}$ straight or branched-chain alkyl; and $R^1$ is hydrogen, or $C_{1-6}$ straight or branched-chain alkyl;

provided that the compound is not:

a) 3,4,5-piperidinetriol, 1-butyl-2-(hydroxymethyl)-, (2S,3R,4R,5S);

b) 3,4,5-piperidinetriol, 1-phenylmethyl-2-(hydroxymethyl)-, (2S,3R,4R,5S);

c) 3,4,5-piperidinetriol, 1-nonyl-2-(hydroxymethyl)-, (2S,3S,4R,5S);

d) 3,4,5-piperidinetriol, 1-dodecyl-2-(hydroxymethyl)-, (2S,3R,4R,5S); or e) 3,4,5-piperidinetriol, 1-(1-phenyl)ethyl-2-(hydroxymethyl)-, (2S,3R,4R,5S).

As described herein, the compounds of the present invention can be used for the inhibition of GCS. Thus, in a second aspect, the present invention provides the use of the compounds of formula (I), but without the provisos a), b), d) and e), in medicine. Specific compounds for use in this aspect of the invention include, in addition to those mentioned above, the compound 3,4,5-piperidinetriol, 1-butyl-2-(hydroxymethyl)-, (2S,3R,4R,5S).

Suitable, pharmaceutically acceptable salts of the compounds of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

Suitable prodrugs of the compounds of formula (I) include, but are not limited to, pharmaceutically acceptable esters such as $C_{1-6}$ alkyl esters.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

The term "alkyl" as used herein whether on its own or as part of a larger group e.g. "alkylaryl", includes both straight and branched chain radicals. The term alkyl also includes those radicals wherein one or more hydrogen atoms are replaced by fluorine.

The compounds of formula (I) can be prepared by art-recognized procedures from known or commercially available starting materials. If the starting materials are unavailable from a commercial source, their synthesis is described herein, or they can be prepared by procedures known in the art.

Specifically, the compounds of formula (I) may be prepared by processes comprising:

(a) reacting a compound of formula (II):

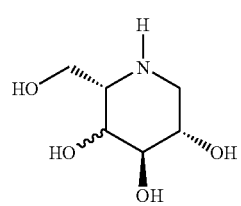

(II)

with $NaBH_3CN$ and an aldehyde of formula $R^2CHO$ in acetic acid-methanol, or with $NaBH(OAc)_3$ and an aldehyde of formula $R^2CHO$ in a solvent such as dichoromethane; wherein $R^2$ is $C_{1-15}$ straight or branched-chain alkyl, optionally substituted by $C_{3-7}$cycloalkyl, and optionally interrupted by —O— the oxygen being separated from the CHO moiety by at least one carbon atom, or $C_{0-9}$alkylaryl where aryl is as defined in formula (I); or (b) deprotection of a compound of formula (III):

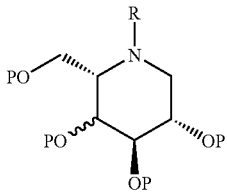
(III)

wherein R is as defined in formula (I), and P, which may be the same or different, are hydroxy protecting groups e.g. benzyl (Bn). When P is CH$_2$Ph the deprotection is conducted in the presence of hydrogen gas and a catalyst such as PdCl$_2$ or palladium on carbon in a suitable solvent such as an alcohol, e.g. ethanol. It will be understood that when P is CH$_2$Ph and R is CH$_2$Ph the R group can also be removed under these conditions to give compounds of formula (II) thus compounds of formula (I) where R is CH$_2$Ph are preferably produced using process a) above.

The compounds of formula (II) are known, see e.g. Carbohydr. Res., 1993, 246, 377-81 (2S3R4R5S) and Tet. Lett., 1997, 38(45), 8009-12 (2S3S4R5S).

Compounds of formula (III) may be prepared by reacting a compound of formula (IV):

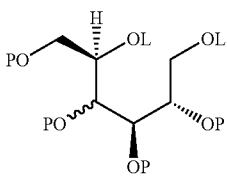
(IV)

wherein L, which may be the same or different are leaving groups, such as mesyl, and P is as defined for formula (III), with an amine of formula RNH$_2$, wherein R is as defined in formula (I), either neat or in a solvent such as tetrahydrofuran.

Compound (IVa), wherein L is mesyl and P is benzyl, is a known compound: V. S. Rao et al., Can. J. Chem., (1981), 59(2), 333-8; P. A. Fowler et al., Carbohydr. Res., (1993), 246, 377-81.

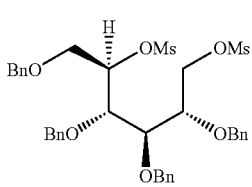
(IVa)

Compound (IVb), wherein L is mesyl and P is benzyl, may be prepared by reacting 2,3,4,6-tetra-O-benzyl-D-galactitol with mesyl chloride in the presence of a base such as pyridine.

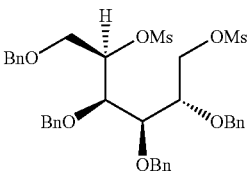
(IVb)

Any novel intermediate compounds as described herein also fall within the scope of the present invention.

Thus according to a further aspect of the invention there is provided a compound of formula (III) as defined above, provided that the compound is not:
i) piperidine, 1-phenylmethyl-3,4,5-tris(phenylmethoxy)-2-[(phenylmethoxy)-methyl], (2S,3R,4R,5S);
ii) piperidine, 1-phenylmethyl-3,4,5-tris(acetyloxy)-2-[(acetyloxy)-methyl], (2S,3R,4R,5S);
iii) piperidine, 1-phenylmethyl-3,4-di(acetyloxy)-5-(phenylmethoxy)-2-[(phenylmethoxy)-methyl], (2S,3S,4R,5S);
iv) piperidine, 1-methyl-3,4-di(acetyloxy)-5-(phenylmethoxy)-2-[(phenylmethoxy)-methyl], (2S,3S,4R,5S);
v) cholestan-3-ol, 1-phenylmethyl-3,4,5-tris(phenylmethoxy)-2-(hydroxymethyl)piperidine, (2S,3R,4R,5S), butanedioate, (3α,5α)-; or
vi) piperidine, 1-phenylmethyl-3,4-di(phenylmethoxy)-2-[(phenylcarbonyloxy)-methyl]-5-phenylcarbonyloxy, (2S,3R,4R,5S).

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

Further details for the preparation of compounds of formula (I) are found in the examples.

The compounds of formula (I) may be prepared singly or as compound libraries comprising at least 2, for example 5 to 500 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable salts thereof.

The pharmaceutically effective compounds of formula (I) and pharmaceutically acceptable salts thereof, may be administered in conventional dosage forms prepared by combining a compound of formula (I) ("active ingredient") with standard pharmaceutical carriers or diluents according to conventional procedures well known in the art. These procedures may involve mixing, granulating and compressing or dissolving the ingredients as appropriate to the desired preparation.

According to a further aspect the present invention provides pharmaceutical formulations comprising one or more compounds of formula (I), but without provisos a), b), d) and e), together with one or more pharmaceutically acceptable carriers or excipients.

The pharmaceutical compositions of the invention may be formulated for administration by any route, and include those in a form adapted for oral, topical or parenteral administration to mammals including humans.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318, (1986).

Pharmaceutical formulations adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may also include other agents conventional in the art having regard to the type of formulation in question, for example those suitable for oral administration may include flavouring agents.

The pharmaceutical formulations according to the invention are preferably adapted for oral administration.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration.

Pharmaceutical formulations may be presented in unit dose forms containing a predetermined amount of active ingredient per dose. Such a unit may contain for example up to 1 g, suitably 10 mg to 600 mg, preferably 50 mg to 300 mg and more preferably 50 mg to 150 mg depending on the condition being treated, the route of administration and the age, weight and condition of the patient. Preferred unit dosage formulations are those containing a daily dose or sub-dose, as herein above recited, or an appropriate fraction thereof, of an active ingredient.

It will be recognized by one of skill in the art that the optimal quantity and spacing of individual dosages of a formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the formula (I) compound given per day for a defined number of days, can be ascertained by those skilled in the art using conventional course of treatment determination tests.

No toxicological effects are indicated when a compound of formula (I) or a pharmaceutically acceptable derivative thereof is administered in the above-mentioned dosage range.

The compounds of the present invention are useful in that they are capable of inhibiting glucosylceramide synthase. Thus, the compounds of the invention can be used in the treatment of various glycolipid storage diseases such as Gaucher's disease, Sandhoff's disease, Tay-Sachs disease, Fabry disease, GM1 gangliosidosis etc. In addition, compounds such as this also can find use in the treatment of conditions in which glycolipid accumulation occurs such as Niemann-Pick disease, mucopolysaccharidoses (MPS I, MPS IIIA, MPS IIIB, MPS VI and MPS VII), mucolipidosis type IV and α-mannosidosis.

The compounds of the present invention can also be used in the treatment of cancers in which glycolipid synthesis is abnormal such as brain tumours, neuroblastoma, malignant melanoma, renal adenocarcinoma and multi-drug resistant cancers in general.

The compounds of the present invention can also be used in the treatment of disease caused by infectious organisms which use cell surface glycolipid as receptors for the infectious organism or toxin produced by the infectious organism.

The compounds of the present invention can also be used in the treatment of disease caused by infectious organisms for which the synthesis of glucosylceramide is an essential or important process such as the pathogenic fungus cryptococcus neoformans.

The compounds of the present invention can also be used in the treatment of disease in which excessive glycolipid synthesis occurs such as but not limited to, atherosclerosis, polycystic kidney disease and diabetic renal hypertrophy.

The compounds of the present invention can also be used in the treatment of neuronal disorders, such as Alzheimer's disease and epilepsy; and neuronal degenerative disease such as Parkinsons' disease The compounds of the present invention can also be used in the treatment of neuronal injury such as spinal cord injuries or stroke.

The compounds of the present invention can also be used in the treatment of obesity.

In additional aspects, therefore, the present invention provides:

(i) the use of a compound of formula (I) but without provisos a) to e), as an inhibitor of glucosylceramide synthase.

(ii) the use of a compound of formula (I) but without provisos a) to e), in the manufacture of a medicament for the treatment of a glycolipid storage disease. Examples of glycolipid storage disease which can be treated include, but are not limited to: Gaucher disease, Sandhoffs disease, Tay-Sachs disease, Fabry disease or GM1 gangliosidosis.

(iii) the use of a compound of formula (I) but without provisos a) to e), in the manufacture of a medicament for the treatment of Niemann-Pick disease types A and C.

(iv) the use of a compound of formula (I) but without provisos a) to e), in the manufacture of a medicament for the treatment of mucopolysaccharidosis type I, mucopolysaccharidosis type IIID, mucopolysaccharidosis type IIIA, mucopolysaccharidosis type VI or mucopolysaccharidosis type VII.

(v) the use of a compound of formula (I) but without provisos a) to e), in the manufacture of a medicament for the treatment of α-mannosidosis or mucolipidosis type IV.

(vi) the use of a compound of formula (I) but without provisos a) to e), in the manufacture of a medicament for the treatment of cancers in which glycolipid synthesis is abnormal, including but not limited to neuronal cancer including neuroblastoma, brain cancer, renal adenocarcinoma, malignant melanoma, multiple myeloma and multi-drug resistant cancers.

(vii) the use of a compound of formula (I) but without provisos a) to e), in the manufacture of a medicament for use in the treatment of Alzheimer's disease, epilepsy or stroke.

(viii) the use of a compound of formula (I) but without provisos a) to e), in the manufacture of a medicament for use in the treatment of Parkinson's disease.

(ix) the use of the compound of formula (I) but without provisos a) to e), in the manufacture of a medicament in the treatment of spinal injury.

(x) the use of a compound of formula (I) but without provisos a) to e), in the manufacture of a medicament for use in the treatment of disease caused by infectious microorganisms which utilize glycolipids on the surface of cells as receptors for the organism itself or toxins produced by the organism.

(xi) the use of a compound of formula (I) but without provisos a) to e), in the manufacture of a medicament for use in the treatment of disease caused by infectious organisms for which the synthesis of glucosylceramide is an essential or important process such as but not limited to pathologies associated with infections of the pathogenic fungus cryptococcus neoformans.

(xii) the use of a compound of formula (I) but without provisos a) to e), in the manufacture of a medicament for use in the treatment of diseases associated with abnormal glycolipid synthesis including but not limited to polycystic kidney disease, diabetic renal hypertrophy and atherosclerosis.

(xiii) the use of a compound formula (I) but without provisos a) to e), in the manufacture of a medicament for the treatment of a condition treatable by the administration of a ganglioside such as GM1 ganglioside. Examples of such conditions are Parkinson's disease, stroke and spinal cord injuries.

(xiv) the use of a compound of formula (I) but without provisos a) to e), in the manufacture of a medicament for reversibly rendering a male mammal infertile.

(xv) the use of a compound of formula (I) but without provisos a) to e), in the manufacture of a medicament for the treatment of obesity, e.g. as an appetite suppressant.

(xvi) a method for the treatment of a glycolipid storage disease, e.g. Gaucher's disease, Sandhoff's disease, Tay-Sachs disease or GM1 gangliosidosis, which comprises the step of administering to a patient an effective amount of a compound of formula (I) but without provisos a) to e).

(xvii) a method for the treatment of Niemann-Pick disease types A and C, which comprises the step of administering to a patient an effective amount of a compound of formula (I) but without provisos a) to e).

(xviii) a method for the treatment of mucopolysaccharidosis type I, mucopolysaccharidosis type IIID, mucopolysaccharidosis type IIIA, mucopolysaccharidosis type VI or mucopolysaccharidosis type VII which comprises the step of administering to a patient an effective amount of a compound of formula (I) but without provisos a) to e).

(xvix) a method for the treatment of α-mannosidosis or mucolipidosis type IV which comprises the step of administering to a patient an effective amount of a compound of formula (I) but without provisos a) to e).

(xx) a method for the treatment of cancers in which glycolipid synthesis is abnormal, including but not limited to neuronal cancer including neuroblastoma, brain cancer, renal adenocarcinoma, malignant melanoma, multiple myeloma and multi-drug resistant cancers which comprises the step of administering to a patient an effective amount of a compound of formula (I) but without provisos a) to e).

(xxi) a method for the treatment of Alzheimer's disease, epilepsy or stroke which comprises the step of administering to a patient an effective amount of a compound of formula (I) but without provisos a) to e).

(xxii) a method for the treatment of Parkinson's disease, which comprises the step of administering to a patient an effective amount of a compound of formula (I) but without provisos a) to e).

(xxiii) a method for the treatment of spinal injury which comprises the step of administering to a patient an effective amount of a compound of formula (I) but without provisos a) to e).

(xxiv) a method for the treatment of disease caused by infectious microorganisms which utilize glycolipids on the surface of cells as receptors for the organism itself or toxins produced by the organism which comprises the step of administering to a patient an effective amount of a compound of formula (I) but without provisos a) to e).

(xxv) a method for the treatment of disease caused by infectious organisms for which the synthesis of glucosylceramide is an essential or important process such as but not limited to pathologies associated with infections of the pathogenic fungus cryptococcus neoformans which comprises the step of administering to a patient an effective amount of a compound of formula (I) but without provisos a) to e).

(xxvi) a method for the treatment of diseases associated with abnormal glycolipid synthesis including but not limited to polycystic kidney disease, diabetic renal hypertrophy and atherosclerosis, which comprises the step of administering to a patient an effective amount of a compound of formula (I) but without provisos a) to e).

(xxvii) a method for the treatment of a condition treatable by the administration of a ganglioside such as GM1 ganglioside, which comprises the step of administering to a patient an effective amount of a compound of formula (I) but without provisos a) to e). Examples of such conditions are Parkinson's disease, stroke and spinal cord injuries.

(xxviii) a method for reversibly rendering a male mammal infertile, which comprises the step of administering to said male mammal an effective amount of a compound of formula (I) but without provisos a) to e).

(xxix) a method for the treatment of obesity, which comprises the step of administering to a patient an effective amount of a compound of formula (I) but without the provisos a) to e).

The invention also provides for the use of a compound of formula (I) but without provisos a) to e) for the treatment of the above mentioned diseases and conditions.

Figure 1: shows representative pathways for the metabolism of glycolipids in mammalian cells. The reaction catalyzed by glucosylceramide synthase, the assembly of uridine diphosphate-glucose and ceramide into glucosylceramide, is shown. Enzyme pathways resulting in the human glycolipid storage diseases, as well as the glucosylceramide synthase reaction inhibited by N-butyldeoxynojirimycin (NB-DNJ) are also represented. Abbreviations: UDP-Glc, uridine diphosphoglucose; Cer, ceramide; Sial, sialic acid; Gal, galactose; GalNAc, N-acetylgalactosamine; Glc, glucose; and Figure 2: shows (a) a thin layer chromatography (TLC) chromatogram of the non-polar lipid fraction extracted from MCF-7 breast carcinoma cells treated for 7 days with 50 μM example 2 compound (1), MCF-7 breast carcinoma cells (2) and (3) represent a glucosylceramide standard; and (b) represents a measure of the glucosylceramide band intensity from the TLC chromatogram relative to background with (1) representing example 2 compound treated sample and (2) the untreated control.

All publications, including, but not limited to, patents and patent applications, cited in this specification, are herein incorporated by reference as if each individual publication were specifically and individually indicated to be incorporated by reference herein as though fully set forth.

The invention will now be described by reference to the following examples which are merely illustrative and are not to be construed as a limitation of the scope of the present invention.

EXAMPLE 1

3,4,5-Piperidinetriol, 1-propyl-2-(hydroxymethyl)-, (2S,3R,4R,5S)

a) 2,3,4,6-Tetra-O-benzyl-1,5-di-O-mesyl-D-glucitol

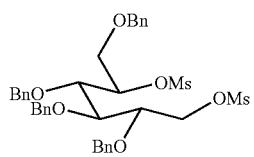 [SMILES: CS(=O)(=O)OCC(OCc1ccccc1)C(OCc1ccccc1)C(OCc1ccccc1)C(COCc1ccccc1)OS(C)(=O)=O]

2,3,4,6-Tetra-O-benzyl-D-glucitol (45 g) was dissolved in pyridine (200 ml) and added over 30 min to a solution of mesyl chloride (15 ml) in pyridine (100 ml) at 0° C. The clear solution was stored at 4° C. overnight, after which time TLC analysis showed completion of the reaction. The reaction mixture was partitioned between ethyl acetate and water/ice. The organic fractions were washed with 5% hydrochloric acid then saturated aqueous sodium bicarbonate solution, dried ($Na_2SO_4$) and concentrated to a yellow/orange oil. The oil was azeotroped with toluene and used directly in the next stage.

b) Piperidine, 1-propyl-3,4,5-tris(phenyl-methoxy)-2-[(phenyl-methoxy)methyl], (2S,3R,4R,5S)

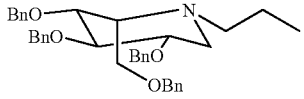

Crude 2,3,4,6-tetra-O-benzyl-1,5-di-O-mesyl-D-glucitol (988 mg) was dissolved in n-propylamine (10 ml) and stirred at 55° C. for 4 days. TLC analysis indicated the reaction had gone to completion. The reaction mixture was concentrated and the resultant crude oil was purified by flash chromatography (gradient elution of 0→16% ethyl acetate/petroleum ether) to give piperidine, 1-propyl-3,4,5-tris(phenylmethoxy)-2-[(phenylmethoxy)-methyl], (2S,3R,4R,5S) (610 mg, 73%). $^1$H NMR (CDCl$_3$): 0.9 (3H, t), 1.4 (2H, m), 2.45 (2H, m), 2.6 (1H, m), 2.8 (1H, dd, J=5, 11 Hz), □δ 3.3 (1H, m), 3.5 (2H, m), 3.6 (2H, m), 3.7 (1H, dd), 4.4-4.8 (8H, m, OCH$_2$Ph), 7.2-7.4 (20H, m, ArH).

c) 3,4,5-Piperidinetriol, 1-propyl-2-(hydroxymethyl)-, (2S,3R,4R,5S)

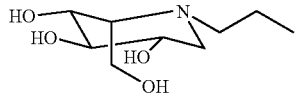

Piperidine, 1-propyl-3,4,5-tris(phenylmethoxy)-2-[(phenylmethoxy)-methyl], (2S,3R,4R,5S) (610 mg) was dissolved in MeOH (10 ml) and stirred overnight under a hydrogen atmosphere in the presence of PdCl$_2$ (300 mg). TLC indicated completion of the reaction. The reaction mixture was filtered through celite (followed by a methanol/water wash) and the filtrate concentrated. The solution was diluted with water (10 ml) and slowly loaded onto 5 g of Dowex 50X4-200 resin that had been pre-washed with hydrochloric acid. The resin was washed with water and then eluted with a mixture of 1:7 conc. aqueous ammonia:water. Product fractions were concentrated to give 3,4,5-piperidinetriol, 1-propyl-2-(hydroxymethyl)-, (2S,3R,4R,5S) (200 mg, 90%) as a gummy solid. $^1$H NMR (D$_2$O): δ 0.75 (3H, t), 1.35 (2H, m), 2.45 (3H, m), 2.75 (1H, dd, J=5, 12.5 Hz), 3.0 (1H, dd, J=4, 9 Hz), 3.3 (1H, t), 3.45 (1H, m), 3.6 (1H, dd, J=5, 10 Hz), 3.7 (2H, m).

EXAMPLE 2

3,4,5-Piperidinetriol, 1-butyl-2-(hydroxymethyl)-, (2S,3R,4R,5S)

a) Piperidine, 1-butyl-3,4,5-tris(phenylmethoxy)-2-[(phenylmethoxy)-methyl], (2S,3R,4R,5S)

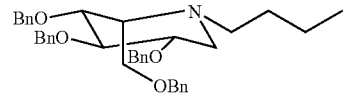

Crude 2,3,4,6-tetra-O-benzyl-1,5-di-O-mesyl-D-glucitol (Example 1a), 30 g) was dissolved in n-butylamine (200 ml) and stirred at 50° C. for 4 days. TLC analysis indicated the reaction had gone to completion. The reaction mixture was concentrated and the resultant crude oil was purified by flash chromatography (gradient elution of 0→16% ethyl acetate/petroleum ether) to give piperidine, 1-butyl-3,4,5-tris(phenylmethoxy)-2-[(phenylmethoxy)-methyl], (2S,3R,4R,5S) (23 g, 90%). $^1$H NMR (CDCl$_3$): δ 0.9 (3H, t), 1.2 (2H, m), 1.4 (2H, m), 2.5 (2H, m), 2.7 (1H, m), 2.9 (1H, dd, J=6, □ 12 Hz), 3.4 (1H, m), 3.5 (1H, AB quartet J=10 Hz), 3.55 (1H, m), 3.65 (1H, m), 3.7 (1H, dd, J=2, 13 Hz), 3.8 (1H, dd, J=6, 10 Hz), 4.4-4.9 (8H, m, OCH$_2$Ph), 7.2-7.4 (20H, m, ArH).

b) 3,4,5-Piperidinetriol, 1-butyl-2-(hydroxymethyl)-, (2S,3R,4R,5S)

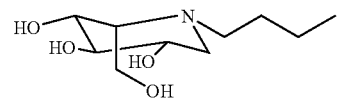

Piperidine, 1-butyl-3,4,5-tris(phenylmethoxy)-2-[(phenylmethoxy)-methyl], (2S,3R,4R,5S) (15 g) was dissolved in MeOH (300 ml) and stirred overnight under a hydrogen atmosphere in the presence of PdCl$_2$ (5 g). TLC indicated completion of the reaction. The reaction mixture was filtered through celite (followed by a methanol/water wash) and the filtrate concentrated to ca. 50 ml. The solution was slowly loaded onto 70 g of Dowex 50X12-200 resin that had been pre-washed with hydrochloric acid. The resin was washed with water and then eluted with a mixture of 1:7 conc. aqueous ammonia:water. Product fractions were concentrated to give 3,4,5-piperidinetriol, 1-butyl-2-(hydroxymethyl)-, (2S,3R,4R,5S) (4.8 g, 85%) as a colourless oil. $^1$H NMR (D$_2$O): δ 0.90 (3H, t), 1.31 (2H, m), 1.49 (2H, m), 2.53 (1H, dd), 2.63 (1H, ddd), 2.72 (1H, ddd), 2.87 (1H, dd), 3.14 (1H, q), 3.44 (1H, t), 3.61 (1H, ddd), 3.75 (1H, dd), 3.85 (1H, dd), 3.89 (1H, dd).

EXAMPLE 3

3,4,5-Piperidinetriol, 1-pentyl-2-(hydroxymethyl)-, (2S,3R,4R,5S)

a) Piperidine, 1-pentyl-3,4,5-tris(phenylmethoxy)-2-[(phenyl-methoxy)methyl], (2S,3R,4R,5S)

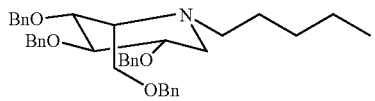

Crude 2,3,4,6-tetra-O-benzyl-1,5-di-O-mesyl-D-glucitol (Example 1a), 1g) was dissolved in n-pentylamine (10 ml) and stirred at 55° C. for 4 days. TLC analysis indicated the reaction had gone to completion. The reaction mixture was concentrated and the resultant crude oil was purified by flash chromatography (gradient elution of 0→12% ethyl acetate/petroleum ether) to give piperidine, 1-pentyl-3,4,5-tris(phenylmethoxy)-2-[(phenylmethoxy)-methyl], (2S,3R,4R,5S) (680 mg, 76%). $^1$H NMR (CDCl$_3$): δ 1.0 (3H, t), 1.2 (2H, m), 1.4 (4H, m), 1.6 (2H, m), 2.7 (2H, m), 2.85 (1H, m), ☐ 3.05 (1H, dd, J=5, 10.5 Hz), 3.55 (1H, m), 3.7 (2H, m), 3.85 (2H, m), 3.95 (1H, dd, J=5, 9 Hz), 4.6-5.05 (8H, m, OCH$_2$Ph), 7.4-7.5 (20H, m, ArH).

b) 3,4,5-Piperidinetriol, 1-pentyl-2-(hydroxymethyl)-, (2S,3R,4R,5S)

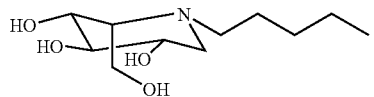 [SMILES: CCCCCN1CC(O)C(O)C(O)C1CO]

Piperidine, 1-pentyl-3,4,5-tris(phenylmethoxy)-2-[(phenylmethoxy)-methyl], (2S,3R,4R,5S) (680 mg) was dissolved in MeOH (10 ml) and stirred overnight under a hydrogen atmosphere in the presence of PdCl$_2$ (300 mg). TLC indicated completion of the reaction. The reaction mixture was filtered through celite (followed by a methanol/water wash) and the filtrate concentrated. The concentrate was diluted with water and slowly loaded onto 5 g of Dowex 50X4-200 resin that had been pre-washed with hydrochloric acid. The resin was washed with water and then eluted with a mixture of 1:7 conc. aqueous ammonia:water. Product fractions were concentrated to give 3,4,5-piperidinetriol, 1-pentyl-2-(hydroxymethyl)-, (2S,3R,4R,5S) (240 mg, 90%) as a gummy solid. $^1$H NMR (D$_2$O): δ 0.75 (3H, t), 1.15 (4H, m), 1.35 (2H, m), 2.35 (1H, dd, J=10, 12.5 Hz), 2.5 (2H, m), 2.7 (1H, dd, J=5, 12 Hz), 3.0 (1H, dd, J=4, 9 Hz), 3.25 (1H, t), 3.45 (1H, m), 3.6 (1H, dd, J=5, 10 Hz), 3.75 (2H, m).

EXAMPLE 4

3,4,5-Piperidinetriol, 1-heptyl-2-(hydroxymethyl)-, (2S,3R,4R,5S)

a) Piperidine, 1-heptyl-3,4,5-tris(phenylmethoxy)-2-[(phenyl-methoxy)methyl], (2S,3R,4R,5S)

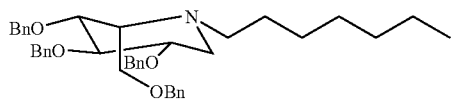

Crude 2,3,4,6-tetra-O-benzyl-1,5-di-O-mesyl-D-glucitol (Example 1a), 1 g) was dissolved in n-heptylamine (10 ml) and stirred at 55° C. for 4 days. TLC analysis indicated the reaction had gone to completion. The reaction mixture was concentrated and the resultant crude oil was purified by flash chromatography (gradient elution of 0→25% diethyl ether/petroleum ether) to give piperidine, 1-heptyl-3,4,5-tris(phenylmethoxy)-2-[(phenylmethoxy)-methyl], (2S,3R,4R,5S) (690 mg, 76%). $^1$H NMR (CDCl$_3$): δ 0.9 (3H, t), 1.3 (8H, m), 1.4 (2H, m), 2.5 (2H, m), 2.7 (1H, m), 2.9 (1H, dd, J=5, ☐ 11 Hz), 3.4 (1H, m), 3.55 (2H, m), 3.7 (2H, m), 3.8 (1H, dd J=6, 13 Hz), 4.4-4.9 (8H, m, OCH$_2$Ph), 7.2-7.4 (20H, m, ArH).

b) 3,4,5-Piperidinetriol, 1-heptyl-2-(hydroxymethyl)-, (2S,3R,4R,5S)

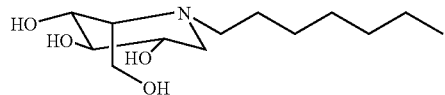 [SMILES: CCCCCCCN1CC(O)C(O)C(O)C1CO]

Piperidine, 1-heptyl-3,4,5-tris(phenylmethoxy)-2-[(phenylmethoxy)-methyl], (2S,3R,4R,5S) (690 mg) was dissolved in MeOH (10 ml) and stirred overnight under a hydrogen atmosphere in the presence of PdCl$_2$ (350 mg). TLC indicated completion of the reaction. The reaction mixture was filtered through celite (followed by a methanol/water wash) and the filtrate concentrated. The concentrate was diluted with water (5 ml) and slowly loaded onto 5 g of Dowex 50X4-200 resin that had been pre-washed with hydrochloric acid. The resin was washed with water and then eluted with a mixture of 1:7 conc. aqueous ammonia:water. Product fractions were concentrated to give 3,4,5-piperidinetriol, 1-heptyl-2-(hydroxymethyl)-, (2S,3R,4R,5S) (260 mg, 90%) as a gummy solid. $^1$H NMR (D$_2$O): δ 0.7 (3H, t), 1.1 (8H, m), 1.3 (2H, m), 2.45 (3H, m), 2.7 (1H, dd, J=5, 10 Hz), 2.95 (1H, dd, J=4, 9 Hz), 3.25 (1H, t), 3.4 (1H, m), 3.55 (1H, dd, J=5.5, 9.5 Hz), 3.65 (2H, m).

EXAMPLE 5

3,4,5-Piperidinetriol, 1-butyl-2-hydroxymethyl)-, (2S,3S,4R,5S)

a) 2,3,4,6-Tetra-O-benzyl-D-galactitol

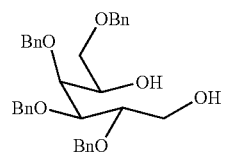

2,3,4,6-Tetra-O-benzyl-D-galactopyranose (107 g) was dissolved in ethanol (0.6 L) and, whilst stirring at 0° C., sodium borohydride (31 g) was added. After stirring overnight TLC analysis indicated completion of the reaction. The ethanol solution was partitioned between water (3 L) and ether (1.5 L). The organic phase was dried ($Na_2SO_4$), filtered and concentrated. The resulting oil was purified by flash chromatography (gradient elution using 20→50% ethyl acetate/petroleum ether) and then crystallised from a mixture of ethyl acetate/petroleum ether to give 2,3,4,6-tetra-O-benzyl-D-galactitol (97 g, 91%) as a white solid. $^1$H NMR ($CDCl_3$): δ 2.4 (1H, bs), 3.35 (1H, bs), 3.55 (2H, m), 3.8 (3H, m), 3.9 (2H, m), 4.1 (1H, m), 4.4-4.8 (8H, m, $OCH_2Ph$), 7.2-7.4 (20H, m, ArH). Mass spectrum: m/z 543 (M+H)$^+$ 565 (M+Na)$^+$.

b) 2,3,4,6-Tetra-O-benzyl-1,5-di-O-mesyl-D-galactitol

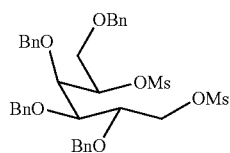 [SMILES: CS(=O)(=O)OCC(OCc1ccccc1)C(OCc1ccccc1)C(OCc1ccccc1)C(COCc1ccccc1)OS(C)(=O)=O]

2,3,4,6-Tetra-O-benzyl-D-galactitol (7.6 g) was stirred at 0° C. in pyridine (20 ml) and a solution of mesyl chloride (2.5 ml) in pyridine (20 ml) was added. The solution was stored at 4° C. overnight. TLC analysis showed completion of the reaction. The reaction mixture was partitioned between ethyl acetate and water/ice. The organic fractions were washed with 5% hydrochloric acid then saturated aqueous sodium bicarbonate solution, dried ($Na_2SO_4$) and concentrated to give a colourless oil which was used directly in the next stage.

c) Piperidine, 1-butyl-3,4,5-tris(phenylmethoxy)-2-[(phenylmethoxy)-methyl], (2S,3S,4R,5S)

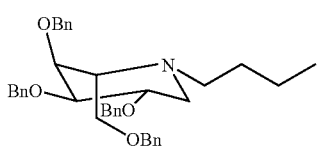 [SMILES: CCCCN1CC(OCc2ccccc2)C(OCc2ccccc2)C(OCc2ccccc2)C1COCc1ccccc1]

The crude 2,3,4,6-tetra-O-benzyl-1,5-di-O-mesyl-D-galactitol was dissolved in n-butylamine (50 ml) and stirred at 55° C. for 5 days. The reaction mixture was concentrated and the crude oil purified by flash chromatography (gradient elution of 5→16% ethyl acetate/petroleum ether) to give piperidine, 1-butyl-3,4,5-tris(phenylmethoxy)-2-[(phenylmethoxy)-methyl], (2S,3S,4R,5S) (4.8 g, 59% from 2,3,4,6-tetra-O-benzyl-1,5-di-O-mesyl-D-galactitol) as a colourless oil. $^1$H NMR ($CDCl_3$): δ 0.9 (t, 3H, J=6 Hz), 1.25 (m, 2H), 1.4 (m, 2H), 2.6 (m, 3H), 2.8 (m, 1H), 3.0 (m, 1H), 3.4 (m, 1H), 3.55 (2H, m), 3.75 (1H, m), 3.8 (1H, m), 4.3-4.6 (8H, m, $OCH_2Ph$), 7.15-7.3 (20H, m, ArH).

d) 3,4,5-Piperidinetriol, 1-butyl-2-hydroxymethyl)-, (2S,3S,4R,5S)

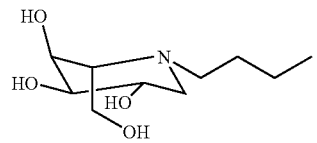

Piperidine, 1-butyl-3,4,5-tris(phenylmethoxy)-2-[(phenylmethoxy)-methyl], (2S,3S,4R,5S) (4.8 g) was dissolved in methanol (100 ml) and stirred overnight under a hydrogen atmosphere in the presence of $PdCl_2$ (2.5 g). TLC indicated completion of the reaction. The reaction mixture was filtered through celite (followed by a methanol/water wash) and concentrated to a 25 ml aqueous solution. This solution was slowly loaded onto 40 ml of Amberlite IR-120 (plus) resin which had been pre-washed with hydrochloric acid. The resin was washed with water then eluted with a mixture of 1:7 conc. aqueous ammonia:water (500 ml). Product fractions were concentrated to give 3,4,5-piperidinetriol, 1-butyl-2-(hydroxymethyl)-, (2S,3S,4R,5S) (1.27 g, 70%) as a colourless oil. $^1$H NMR ($D_2O$): δ 0.95 (3H, t), 1.35 (m, 2H), 2.61 (1H, dd), 2.70 (1H, m), 2.87 (1H, dd), 2.95 (1H, ddd), 3.76 (1H, ddd), 3.78 (1H, dd), 3.90 (1H, dd), 3.94 (1H, ddd), 4.06 (1H, dd).

EXAMPLE 6

3,4,5-Piperidinetriol, 1-nonyl-2-(hydroxymethyl)-, (2S,3R,4R,5S)

a) Piperidine, 1-nonyl-3,4,5-tris(phenylmethoxy)-2-[(phenylmethoxy)methyl], (2S,3R,4R,5S)

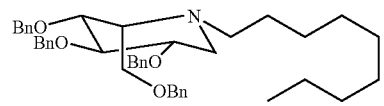 [SMILES: CCCCCCCCCN1CC(OCc2ccccc2)C(OCc2ccccc2)C(OCc2ccccc2)C1COCc1ccccc1]

Crude 2,3,4,6-tetra-O-benzyl-1,5-di-O-mesyl-D-glucitol (Example 1a), 1.0 g) was dissolved in nonylamine (1.2 ml) and stirred at 55° C. for 5 days. The reaction mixture was concentrated and the resultant crude oil was purified by column chromatography (gradient elution 0→12% ethyl ether/petroleum ether) to give piperidine, 1-nonyl-3,4,5-tris(phenylmethoxy)-2-[(phenylmethoxy)methyl], (2S,3R,4R,5S) (660 mg, 71%). $^1$H NMR (300 MHz, $CDCl_3$) δ 0.88 (3H, t, J 7 Hz); 1.14-1.40 (12H, m); 1.40-1.55 (2H, m); 2.43-2.54 (2H, m); 2.60-2.71 (1H, m); 2.84 (1H, dd, J=12, 5 Hz); 3.30-3.36 (1H, m); 3.42-3.57 (2H, m); 3.64 (1H, dd, 9, 5 Hz); 3.67 (1H, dd, J=11, 3 Hz); 3.78 (1H, dd, J=9, 6 Hz); 4.47 (2H, ABq); 4.56-4.72 (4H, m); 4.78 (2H, ABq); 7.18-7.42 (20H, m).

b) 3,4,5-Piperidinetriol, 1-nonyl-2-(hydroxymethyl)-, (2S,3R,4R,5S)

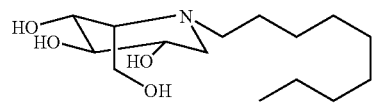 [SMILES: CCCCCCCCCN1CC(O)C(O)C(O)C1CO]

Piperidine, 1-nonyl-3,4,5-tris(phenylmethoxy)-2-[(phenylmethoxy)-methyl], (2S,3R,4R,5S) (660 mg) was dissolved in MeOH (10 ml) and stirred overnight under a hydrogen atmosphere in the presence of $PdCl_2$ (300 mg). The reaction mixture was filtered through celite (followed by a methanol/water wash) and the filtrate was concentrated. The concentrate was purified by absorption onto Dowex 50X4-200 resin (8 g) and elution with a mixture of 1:7 aqueous ammonia:water to give 3,4,5-piperidinetriol, 1-nonyl-2-(hydroxymethyl)-, (2S,3R,4R,5S) (160 mg, 61%) as a gummy solid. $^1$H NMR (300 MHz, $CD_3OD$) δ 0.91 (3H, m); 1.3 (12H, bs); 1.45-1.58 (2H, m); 2.53-2.69 (2H, m); 2.70-2.84 (2H, m); 3.00-3.07 (1H, m); 3.35-3.42 (1H, m); 3.49-3.58 (1H, m); 3.70 (1H, dd, J=9, 5 Hz); 3.78-3.89 (2H, m). MS m/z 290.4 $(M+H)^+$.

EXAMPLE 7

3,4,5-Piperidinetriol, 1-(1-ethyl)propyl-2-(hydroxymethyl)-, (2S,3R,4R,5S)

a) Piperidine, 1-(1-ethyl)propyl-3,4,5-tris(phenylmethoxy)-2-[(phenylmethoxy)methyl], (2S,3R,4R,5S)

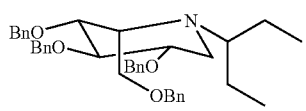

1,5-Di-O-methanesulfonyl-2,3,4,6-tetra-O-benzyl-D-glucitol (4.0 g) was dissolved in 1-ethylpropylamine (6 ml) and stirred at 55° C. for 4 days. The reaction mixture was concentrated and the resultant brown oil was purified by column chromatography on silica gel (gradient elution 0 to 15% diethyl ether/petroleum ether) to give piperidine, 1-(1-ethyl)propyl-3,4,5-tris(phenylmethoxy)-2-[(phenylmethoxy)methyl], (2S,3R,4R,5S) (1.46 g, 33%) as a pale yellow oil. $^1$H NMR ($CDCl_3$): 0.79-0.86 (6H, m), 1.17-1.30 (4H, m), 2.30-2.41 (1H, m), 2.62-2.71 (1H, m), 2.83 (1H, dd, J=12, 5 Hz), 3.30-3.34 (1H, m), 3.43-3.53 (2H, m), 3.66-3.73 (2H, m), 3.83 (1H, dd, J=9, 6 Hz), 4.50 (2H, s), 4.63-4.79 (4H, m), 4.83 (2H, ABq), 7.23-7.42 (20H, m).

b) 3,4,5-Piperidinetriol, 1-(1-ethyl)propyl-2-(hydroxymethyl)-, (2S,3R,4R,5S)

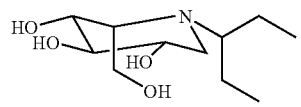

To a solution of piperidine, 1-(1-ethyl)propyl-3,4,5-tris(phenylmethoxy)-2-[(phenyl-methoxy)methyl], (2S,3R,4R, 5S) (1.46 g) in methanol (15 ml) was added $PdCl_2$ (750 mg). The reaction mixture was stirred under an atmosphere of hydrogen overnight. TLC analysis indicated completion of the reaction and it was filtered through a celite pad and concentrated. The crude material was purified by absorption onto 8.5 g of Dowex 50X4-200 resin and elution with a mixture of 1:7 28% aqueous ammonia:water gave, after lyophilisation, 3,4,5-piperidinetriol, 1-(1-ethyl)propyl-2-(hydroxymethyl)-, (2S,3R,4R,5S) (530 mg, 92%) as a white solid. $^1$H NMR ($D_2O$): 0.82 (6H, t, J=7 Hz), 1.29-1.58 (4H, m), 2.41-2.52 (2H, m), 2.87 (1H, dd, J=13, 5 Hz), 3.16 (1H, dd, J 10, 4 Hz), 3.36-3.44 (1H, m), 3.47-3.56 (1H, m), 3.69-3.77 (3H, m). MS m/z 234 $(M+H)^+$.

EXAMPLE 8

3,4,5-Piperidinetriol, 1-(3-methyl)butyl-2-(hydroxymethyl)-, (2S,3R,4R,5S)

a) Piperidine, 1-(3-methyl)butyl-3,4,5-tris(phenylmethoxy)-2-[(phenylmethoxy)methyl], (2S,3R,4R, 5S)

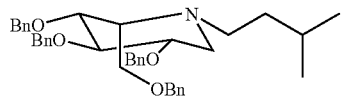 [SMILES: CC(C)CCN1CC(OCc2ccccc2)C(OCc2ccccc2)C(OCc2ccccc2)C1COCc1ccccc1]

1,5-Di-O-methanesulfonyl-2,3,4,6-tetra-O-benzyl-D-glucitol (4.0 g) was dissolved in isoamylamine (4 ml) and stirred at 55° C. for 4 days. The reaction mixture was concentrated and the resultant brown oil was purified by column chromatography on silica gel (gradient elution 0 to 20% diethyl ether/petroleum ether) to give piperidine, 1-(3-methyl)butyl-3,4,5-tris(phenylmethoxy)-2-[(phenylmethoxy)methyl], (2S, 3R,4R,5S) (2.53 g, 67%) as a colourless oil. $^1$H NMR ($CDCl_3$): 0.80 (6H, d, J=6 Hz), 1.12-1.33 (3H, m), 2.39-2.50 (2H, m), 2.59-2.70 (1H, m), 2.79 (1H, dd, J=11, 4 Hz), 3.26-3.32 (1H, m), 3.38-3.52 (2H, m), 3.56-3.67 (2H, m), 3.74 (1H, dd, J=11, 6 Hz), 4.43 (2H, ABq), 4.52-4.67 (4H, m), 4.75 (2H, ABq), 7.18-7.30 (20H, m).

b) 3,4,5-Piperidinetriol, 1-(3-methyl)butyl-2-(hydroxymethyl)-, (2S,3R,4R,5S)

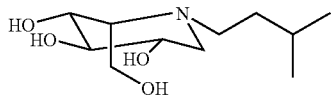 [SMILES: CC(C)CCN1CC(O)C(O)C(O)C1CO]

To a solution of piperidine, 1-(3-methyl)butyl-3,4,5-tris(phenylmethoxy)-2-[(phenylmethoxy)methyl], (2S,3R,4R,5S) (2.53 g) in methanol (30 ml) was added PdCl$_2$ (1.2 g). The reaction mixture was stirred under an atmosphere of hydrogen overnight. TLC analysis indicated completion of the reaction and it was filtered through a celite pad and concentrated. The crude material was purified by absorption onto 12 g of Dowex 50X4-200 resin and elution with a mixture of 1:7 28% aqueous ammonia:water gave 3,4,5-piperidinetriol, 1-(3-methyl)butyl-2-(hydroxymethyl)-, (2S,3R,4R,5S) (960 mg, 97%) as a gummy solid. $^1$H NMR (D$_2$O): 0.83 (6H, dd, J=7, 1 Hz), 1.26-1.42 (2H, m), 1.43-1.55 (1H, m), 2.46 (1H, dd, J☐=12, 10 Hz), 2.57 (1H, ddd, J=12, 10, 6 Hz), 2.68 (1H, ddd, J=12, 10, 6 Hz), 2.81 (1H, dd, J=12, 5 Hz), 3.08 (1H, dd, J=10, 5 Hz), 3.36 (1H, t, J=9 Hz), 3.54 (1H, ddd, J=10, 9, 5 Hz), 3.68 (1H, dd, J=10, 6 Hz), 3.75-3.87 (2H, m). MS m/z 234 (M+H)$^+$.

EXAMPLE 9

3,4,5-Piperidinetriol, 1-(2-phenyl)ethyl-2-(hydroxymethyl)-, (2S,3R,4R,5S)

a) Piperidine, 1-(2-phenyl)ethyl-3,4,5-tris(phenylmethoxy)-2-[(phenylmethoxy)methyl],(2S,3R,4R,5S)

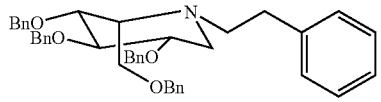 [SMILES: c1ccc(CCN2CC(OCc3ccccc3)C(OCc3ccccc3)C(OCc3ccccc3)C2COCc2ccccc2)cc1]

1,5-Di-O-methanesulfonyl-2,3,4,6-tetra-O-benzyl-D-glucitol (5.0 g) was dissolved in phenethylamine (10 ml) and stirred at 55° C. for 3 days. The reaction mixture was concentrated and the resultant brown oil was purified by column chromatography on silica gel (gradient elution 0 to 30% diethyl ether/petroleum ether) to give piperidine, 1-(2-phenyl)ethyl-3,4,5-tris(phenylmethoxy)-2-[(phenylmethoxy)methyl], (2S,3R,4R,5S) (3.2 g, 71%) of as a colourless oil. $^1$H NMR (CDCl$_3$): 0.86-0.98 (2H, m), 1.16-1.28 (2H, m), 2.56-2.7 (1H, m), 2.70-2.88 (1H, m), 2.91 (1H, ☐ dd, J=11, 4 Hz), 2.98-3.06 (1H, m), 3.41-3.46 (1H, m), 3.46-3.60 (2H, m); 3.66 (1H, dd, J=9, 6 Hz); 3.75 (1H, dd, J 10, 3 Hz), 3.87 (1H, dd, J=10, 6 Hz), 4.52 (2H, ABq), 4.60-4.74 (4H, m), 4.83 (2H, ABq), 7.10-7.38 (25H, m).

b) 3,4,5-Piperidinetriol, 1-(2-phenyl)ethyl-2-(hydroxymethyl)-, (2S,3R,4R,5S)

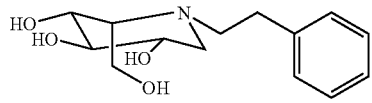

To a solution of piperidine, 1-(2-phenyl)ethyl-3,4,5-tris(phenylmethoxy)-2-[(phenylmethoxy)methyl],(2S,3R,4R,5S) (4.0 g) in methanol (30 ml) was added PdCl$_2$ (1.4 g). The reaction mixture was stirred under an atmosphere of hydrogen overnight. TLC analysis indicated completion of the reaction and it was filtered through a celite pad and concentrated. The crude material was absorbed onto 20 g of Dowex 50X4-200 resin and eluted with a mixture of 1:7 28% aqueous ammonia:water. The product fractions were lyophilised and then purified by column chromatography on silica gel (gradient elution 0 to 20% MeOH/dichloromethane) to give 3,4,5-piperidinetriol, 1-(2-phenyl)ethyl-2-(hydroxymethyl)-, (2S,3R,4R,5S) (970 mg, 81%) as a gummy solid. $^1$H NMR (D$_2$O): 2.50 (1H, dd, J=12, 10 Hz), 2.68-2.97 (5H, m), 3.3 (1H, dd, J=9, 5 Hz), 3.36 (1H, ☐ t, J=9 Hz), 3.51-3.61 (1H, m), 3.66-3.73 (2H, m), 3.74-3.83 (1H, m), 7.18-7.37 (5H, m). MS m/z 268 (M+H)$^+$.

EXAMPLE 10

3,4,5-Piperidinetriol, 1-(3-phenyl)propyl-2-(hydroxymethyl)-, (2S,3R,4R,5S)

a) Piperidine, 1-(3-phenyl)propyl-3,4,5-tris(phenylmethoxy)-2-[(phenylmethoxy)methyl],(2S,3R,4R,5S)

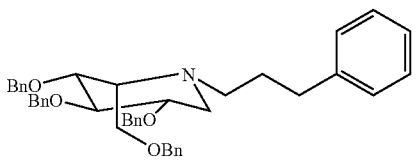 [SMILES: c1ccc(CCCN2CC(OCc3ccccc3)C(OCc3ccccc3)C(OCc3ccccc3)C2COCc2ccccc2)cc1]

1,5-Di-O-methanesulfonyl-2,3,4,6-tetra-O-benzyl-D-glucitol (5.0 g) was dissolved in 3-phenylpropylamine (5 ml) and stirred at 55° C. for 3 days. The reaction mixture was concentrated and the resultant brown oil was purified by column chromatography on silica gel (gradient elution 0 to 25% diethyl ether/petroleum ether) to give piperidine, 1-(3-phenyl)propyl-3,4,5-tris(phenylmethoxy)-2-[(phenylmethoxy)methyl], (2S,3R,4R,5S) (4.25 g, 100%) as a pale yellow oil. $^1$H NMR (CDCl$_3$): 1.72-1.84 (2H, m), 2.54-2.64 (4H, m), 2.70-2.80 (1H, m), 2.87 (1H, dd, J=11, ☐ 5 Hz), 3.34-3.39 (1H, m), 3.46-3.62 (2H, m), 3.65-3.74 (2H, m), 3.84 (1H, dd, J=10, 6 Hz), 4.52 (2H, ABq), 4.62-4.75 (4H, m), 4.84 (2H, ABq), 7.12-7.39 (25H, m).

b) 3,4,5-Piperidinetriol, 1-(3-phenyl)propyl-2-(hydroxymethyl)-, (2S,3R,4R,5S)

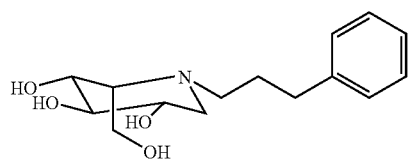 [SMILES: OCC1C(O)C(O)C(O)CN1CCCc1ccccc1]

To a solution of piperidine, 1-(3-phenyl)propyl-3,4,5-tris(phenylmethoxy)-2-[(phenylmethoxy)methyl],(2S,3R,4R,5S) (4.2 g) in methanol (40 ml) was added PdCl$_2$ (1.6 g). The reaction mixture was stirred under an atmosphere of hydrogen overnight. TLC analysis indicated completion of the reaction and it was filtered through a celite pad and concentrated. The crude material was absorbed onto 20 g of Dowex 50X4-200 resin and eluted with a mixture of 1:7 28% aqueous ammonia:water. The product fractions were lyophilised and then purified by column chromatography on silica gel (gradient elution 0 to 20% MeOH/dichloromethane) to give 3,4,5-piperidinetriol, 1-(3-phenyl)propyl-2-(hydroxymethyl)-, (2S,3R,4R,5S) (1.36 g, 71%) of as a clear gum. $^1$H NMR (D$_2$ 1.69-1.82 (2H, m), 2.44 (1H, dd, ☐ O): J=12, 10 Hz), 2.51-2.72 (4H, m), 2.78 (1H, dd, J=13, 5 Hz), 3.05 (1H, dd, J=11, 5 Hz), 3.34 (1H, t, J=9 Hz), 3.52 (1H, ddd, J=10, 9, 5 Hz), 3.66 (1H, dd, J=10, 5 Hz), 3.71-3.81 (2H, m), 7.17-7.35 (5H, m). MS m/z 282 (M=H)$^+$.

EXAMPLE 11

3,4,5-Piperidinetriol, 1-(1-ethyl)hexyl-2-(hydroxymethyl)-, (2S,3R,4R,5S)

a) Piperidine, 1-(2-ethyl)hexyl-3,4,5-tris(phenylmethoxy)-2-[(phenylmethoxy)methyl],(2S,3R,4R,5S)

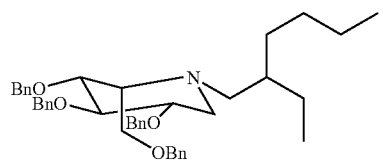 [SMILES: CCCCC(CC)CN1CC(OCc2ccccc2)C(OCc2ccccc2)C(OCc2ccccc2)C1COCc1ccccc1]

1,5-Di-O-methanesulfonyl-2,3,4,6-tetra-O-benzyl-D-glucitol (5.0 g) was dissolved in 2-ethylhexylamine (5 ml) and stirred at 55° C. for 4 days. The reaction mixture was concentrated and the resultant brown oil was purified by column chromatography on silica gel (gradient elution 0 to 17.5% diethyl ether/petroleum ether) to give piperidine, 1-(2-ethyl)hexyl-3,4,5-tris(phenylmethoxy)-2-[(phenylmethoxy)methyl], (2S,3R,4R,5S) (2.6 g, 57%) as a colourless oil. $^1$H NMR (CDCl$_3$): 0.75-0.93 (6H, m), 1.17-1.38 (9H, m), 2.16 (1H, dd, J=13, 6 Hz), 2.25-2.36 (2H, ☐m), 2.52-2.60 (1H, m), 3.02-3.09 (1H, m), 3.24-3.36 (2H, m), 3.40-3.51 (2H, m), 3.60 (1H, dd, J=10, 6 Hz), 4.53 (2H, ABq), 4.62-4.76 (4H, m), 4.85 (2H, ABq), 7.18-7.31 (20H, m).

b) 3,4,5-Piperidinetriol, 1-(2-ethyl)hexyl-2-(hydroxymethyl)-, (2S,3R,4R,5S)

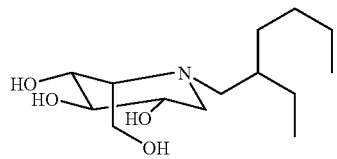 [SMILES: CCCCC(CC)CN1CC(O)C(O)C(O)C1CO]

To a solution of piperidine, 1-(2-ethyl)hexyl-3,4,5-tris (phenylmethoxy)-2-[(phenylmethoxy)methyl], (2S,3R,4R, 5S) (2.6 g) in methanol (20 ml) was added PdCl$_2$ (900 mg). The reaction mixture was stirred under an atmosphere of hydrogen overnight. TLC analysis indicated completion of the reaction and it was filtered through a celite pad and concentrated. The crude material was absorbed onto 13 g of Dowex 50X4-200 resin and eluted with a mixture of 1:7 28% aqueous ammonia:water. The product fractions were then purified by column chromatography on silica gel (gradient elution 0 to 10% MeOH/dichloromethane) to give, after lyophilisation, 3,4,5-piperidinetriol, 1-(1-ethyl)hexyl-2-(hydroxymethyl)-, (2S,3R,4R,5S) (320 mg, 28%) as a gummy solid. $^1$H NMR (CDCl$_3$): 0.68-0.80 (6H, m), 1.08-1.32 (9H, m), 2.30-2.46 (3H, m), 2.60 (1H, dd, J=13, ☐5 Hz), 2.90 (1H, dd, J=12, 6 Hz), 3.30-3.38 (1H, m), 3.40-3.49 (1H, m), 3.55 (1H, dd, J=13, 9 Hz), 3.66 (1H, dd, J=9, 5 Hz), 3.74 (1H, dd, J=11, 7 Hz). MS m/z 276 (M+H)$^+$.

EXAMPLE 12

3,4,5-Piperidinetriol, 1-(2-ethyl)butyl-2-(hydroxymethyl)-, (2S,3R,4R,5S)

a) Piperidine, 1-(2-ethyl)butyl-3,4,5-tris(phenylmethoxy)-2-[(phenylmethoxy)methyl],(2S,3R,4R,5S)

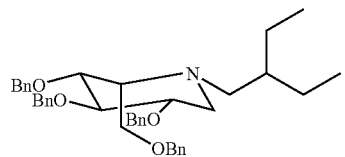 [SMILES: CCC(CC)CN1CC(OCc2ccccc2)C(OCc2ccccc2)C(OCc2ccccc2)C1COCc1ccccc1]

1,5-Di-O-methanesulfonyl-2,3,4,6-tetra-O-benzyl-D-glucitol (3.0 g) was dissolved in 2-ethylbutylamine (2.5 ml) and stirred at 55° C. for 4 days. The reaction mixture was concentrated and the resultant brown oil was purified by column chromatography on silica gel (gradient elution 0 to 12% diethyl ether/petroleum ether) to give piperidine, 1-(2-ethyl) butyl-3,4,5-tris(phenylmethoxy)-2-[(phenylmethoxy)methyl], (2S,3R,4R,5S) (1.93 g, 74%) as a colourless oil (R$_f$: 0.25, 20% ethylacetate/petroleum ether) which was used directly in the next stage.

b) 3,4,5-Piperidinetriol, 1-(2-ethyl)butyl-2-(hydroxymethyl)-, (2S,3R,4R,5S)

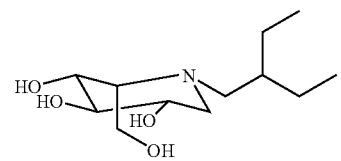 [SMILES: CCC(CC)CN1CC(O)C(O)C(O)C1CO]

To a solution of piperidine, 1-(2-ethyl)butyl-3,4,5-tris(phenylmethoxy)-2-[(phenylmethoxy)methyl], (2S,3R,4R,5S) (1.93 g) in methanol (20 ml) was added PdCl$_2$ (800 mg). The reaction mixture was stirred under an atmosphere of hydrogen overnight. TLC analysis indicated completion of the reaction and it was filtered through a celite pad and concentrated. The crude material was purified by absorption onto 10 g of Dowex 50X4-200 resin and elution with a mixture of 1:7 28% aqueous ammonia:water gave, after lyophilisation, 3,4, 5-piperidinetriol, 1-(2-ethyl)butyl-2-(hydroxymethyl)-, (2S, 3R,4R,5S) (735 mg, 94%) as a white solid. $^1$H NMR (CDCl$_3$): 0.78 (6H, t, J=7 Hz), 1.14-1.30 (5H, m), 2.32-2.48 (3H, m), 2.63 (1H, dd, J=13, ☐ 5 Hz), 2.92 (1H, dd, J=13, 6 Hz), 3.37

(1H, t, J=9 Hz), 3.47 (1H, ddd, J=10, 9, 4 Hz), 3.57 (1H, dd, J=11, 7 Hz), 3.68 (1H, dd, J=9, 6 Hz), 3.77 (1H, dd, J=11, 4 Hz). MS m/z 248 (M+H)⁺.

EXAMPLE 13

3,4,5-Piperidinetriol, 1-[(2R)-(2-methyl-2-phenyl) ethyl]-2-(hydroxymethyl)-, (2S,3R,4R,5S)

a) Piperidine, 1-[(2R)-(2-methyl-2-phenyl)ethyl]-3,4, 5-tris(phenylmethoxy)-2-[(phenylmethoxy)methyl], (2S,3R,4R,5S)

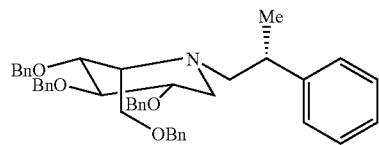 [SMILES: C[C@@H](CN1CC(OCc2ccccc2)C(OCc2ccccc2)C(OCc2ccccc2)C1COCc1ccccc1)c1ccccc1]

1,5-Di-O-methanesulfonyl-2,3,4,6-tetra-O-benzyl-D-glucitol-methyl phenethylamine □ (2.5 g) was dissolved in DMF (3 ml). Diisopropylethylamine (1.5 ml) and R(+)-(1 g) were added and the reaction was stirred at 55° C. for 5 days. The reaction mixture was concentrated and the resultant brown oil was purified by column chromatography on silica gel (gradient elution 0 to 25% diethyl ether/petroleum ether) to give piperidine, 1-[(2R)-(2-methyl-2-phenyl)ethyl]-3,4,5-tris (phenylmethoxy)-2-[(phenylmethoxy)-methyl], (2S,3R,4R, 5S) (740 mg, 32%) as a pale yellow oil. ¹H NMR (CDCl₃): 1.21-1.27 (3H, m), 2.52-2.59 (1H, m), 2.70-2.95 (4H, m), 3.35-3.40 (1H, m), □ 3.44-3.52 (2H, m), 3.64 (1H, dd, J=12, 9 Hz), 3.74 (1H, dd, J=11, 2 Hz), 3.86 (1H, dd, J=9, 6 Hz), 4.47-4.69 (6H, m), 4.83 (2H, ABq), 7.17-7.37 (25H, m).

b) 3,4,5-Piperidinetriol, 1-[(2R)-(2-methyl-2-phenyl) ethyl]-2-(hydroxymethyl)-, (2S,3R,4R,5S)

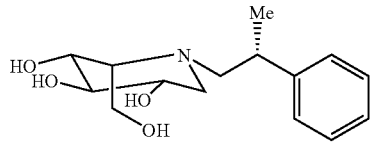 [SMILES: C[C@@H](CN1CC(O)C(O)C(O)C1CO)c1ccccc1]

To a solution of piperidine, 1-[(2R)-(2-methyl-2-phenyl) ethyl]-3,4,5-tris(phenylmethoxy)-2-[(phenylmethoxy)methyl], (2S,3R,4R,5S) (740 mg) in methanol (15 ml) was added PdCl₂ (300 mg). The reaction mixture was stirred under an atmosphere of hydrogen overnight. TLC analysis indicated completion of the reaction and it was filtered through a celite pad and concentrated. The crude material was purified by absorption onto 10 g of Dowex 50X4-200 resin and elution with a mixture of 1:7 28% aqueous ammonia:water gave, after lyophilisation, 3,4,5-piperidinetriol, 1-[(2R)-(2-methyl-2-phenyl)ethyl]-2-(hydroxymethyl)-, (2S,3R,4R,5S) (300 mg, 92%) of as a gummy solid. ¹H NMR (CDCl₃ 1.18 (3H, d, J=5 Hz), 2.42 (1H, dd, J=12, 9 Hz), □ □): 2.56-2.87 (5H, m), 3.29 (1H, t, J=9 Hz), 3.39-3.66 (4H, m), 7.07-7.23 (5H, m). MS m/z 282.3 (M+H)⁺.

EXAMPLE 14

3,4,5-piperidinetriol, 1-[(2S)-(2-methyl-2-phenyl) ethyl]-2-(hydroxymethyl)-, (2S,3R,4R,5S)

a) Piperidine, 1-[(2S)-(2-methyl-2-phenyl)ethyl]-3,4, 5-tris(phenylmethoxy)-2-[(phenylmethoxy)methyl], (2S,3R,4R,5S)

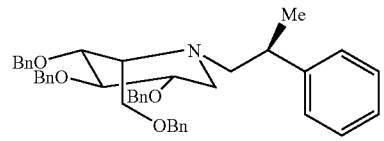 [SMILES: C[C@H](CN1CC(OCc2ccccc2)C(OCc2ccccc2)C(OCc2ccccc2)C1COCc1ccccc1)c1ccccc1]

1,5-Di-O-methanesulfonyl-2,3,4,6-tetra-O-benzyl-D-glucitol-methyl phenethylamine □ (2.5 g) was dissolved in DMF (3 ml). Diisopropylethylamine (1.5 ml) and S(−)-(1g) were added and the reaction was stirred at 55° C. for 5 days. The reaction mixture was partitioned between aqueous NaOH (1 M, 30 ml) and ethyl acetate (50 ml). The organic phase was washed with saturated aqueous NaHCO₃, dried over Na₂SO₄ and concentrated. The resultant crude oil was purified by column chromatography on silica gel (gradient elution 0 to 17% diethyl ether/petroleum ether) to give piperidine, 1-[(2S)-(2-methyl-2-phenyl)ethyl]-3,4,5-tris(phenylmethoxy)-2-[(phenylmethoxy)-methyl], (2S,3R,4R,5S) (700 mg, 31%) as a pale yellow oil. ¹H NMR (CDCl₃): 1.17-1.21 (3H, m), 2.55-2.64 (1H, m), 2.79 (1H, dd, J=12, 7 Hz), 2.87 (1H, dd, J□=13, 6 Hz), 2.98 (1H, dd, J=13, 7 Hz), 3.20-3.26 (1H, m), 3.40-3.54 (3H, m), 3.69 (1H, dd, J=10, 2 Hz), 3.84 (1H, dd, J=13, 7 Hz), 4.46-4.70 (6H, m), 4.8 (2H, ABq), 7.09-7.38 (25H, m).

b) 3,4,5-Piperidinetriol, 1-[(2S)-(2-methyl-2-phenyl) ethyl]-2-(hydroxymethyl)-, (2S,3R,4R,5S)

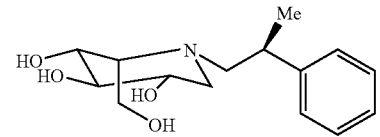 [SMILES: C[C@H](CN1CC(O)C(O)C(O)C1CO)c1ccccc1]

To a solution of piperidine, 1-[(2S)-(2-methyl-2-phenyl) ethyl]-3,4,5-tris(phenylmethoxy)-2-[(phenylmethoxy)methyl], (2S,3R,4R,5S) (700 mg) in methanol (15 ml) was added of PdCl₂ (300 mg). The reaction mixture was stirred under an atmosphere of hydrogen overnight. TLC analysis indicated completion of the reaction and it was filtered through a celite pad and concentrated. The crude material was purified by absorption onto 10 g of Dowex 50X4-200 resin and elution with a mixture of 1:7 28% ammonia:water gave, after lyophilisation, 3,4,5-piperidinetriol, 1-[(2S)-(2-methyl-2-phenyl) ethyl]-2-(hydroxymethyl)-, (2S,3R,4R,5S) (250 mg, 81%) as a gummy solid. ¹H NMR (CDCL₃ 1.17 (3H, d, J=5 Hz), 2.45 (1H, dd, J=13, 10 Hz), 2.59 (1H, □); dd, J=13, 4 Hz), 2.64-2.86 (3H, m), 2.95 (1H, dd, J=14, 6 Hz), 3.34 (1H, t, J=8 Hz), 3.42-3.55 (2H, m), 3.64 (1H, dd, J=8, 5 Hz), 3.74 (1H, dd, J=11, 6 Hz), 7.08-7.23 (5H, m). MS m/z 282.3 (M+H)⁺.

EXAMPLE 15

Piperidine, 1-[(4-methoxyphenyl)methyl]-3,4,5-tris(phenylmethoxy)-2-[(phenylmethoxy)methyl], (2S,3R,4R,5S) [protected intermediate]

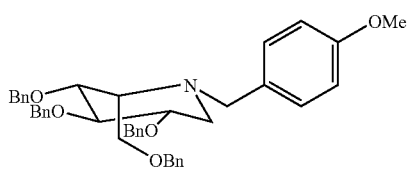 [SMILES: COc1ccc(CN2CC(OCc3ccccc3)C(OCc3ccccc3)C(OCc3ccccc3)C2COCc2ccccc2)cc1]

1,5-Di-O-methanesulfonyl-2,3,4,6-tetra-O-benzyl-D-glucitol (25 g) was dissolved in 4-methoxybenzylamine (50 ml) and stirred at 55° C. for 4 days. The reaction mixture was concentrated and the resultant brown oil was purified by column chromatography on silica gel (gradient elution 0 to 23% diethyl ether/petroleum ether) to give piperidine, 1-[(4-methoxylphenyl)methyl]-3,4,5-tris(phenylmethoxy)-2-[(phenyl-methoxy)methyl], (2S,3R,4R,5S) (17.1 g, 75%) as a pale yellow oil. $^1$H NMR (CDCl$_3$): 2.50-2.60 (1H, m), 2.83 (1H, dd, J=13, 4 Hz), 3.39-3.44 (1H, m), 3.51-3.61 (2H, □m), 3.64-3.80 (3H, m), 3.84 (3H, s), 3.70-3.77 (2H, m), 4.54 (2H, s), 4.58-4.69 (4H, m), 4.85 (2H, ABq), 6.87 (2H, d, J=7 Hz), 7.18 (2H, d, J=7 Hz), 7.26-7.40 (20H, m).

Biological Data

The compounds of the invention were assayed (Table 1) to determine their IC$_{50}$ concentrations against galactosidase and glucosylceramide synthase. In the former case, assays were carried out according to the methods described in Jacob and Scudder, Methods in Enzymology, (1994), 230, 280. In the case of glucosylceramide synthase, assays were carried out according to the method described in Platt et al, J. Biol. Chem., (1994), 269, 27108.

TABLE 1

| A. | Jack bean β-galactosidase (IC$_{50}$ μM) | Mouse ceramide β-galactosidase (IC$_{50}$ μM) | orcine intestinal lactase (Ki μM) | Coffee bean α-galactosidase (IC$_{50}$ μM) | Glucosyl ceramide synthase (IC$_{50}$ μM) |
|---|---|---|---|---|---|
| B. | | | | | |

TABLE 1-continued

| C. | 3.4 | 370 | 85 | 12.6 | 32.5 |
|---|---|---|---|---|---|
| Example 5 | 280 | Not inhibitory | 8000 | 72 | 73.1 |

Table 2 shows data for human enzymes. The assay for inhibition of GCS was performed essentially as described in Platt et al, J. Biol. Chem., (1994), 269, 27108, the enzyme source being human recombinant GCS expressed in insect cells. The glucosidase assays were performed as described (Biochemical Genetics, A Laboratory Manual, Oxford University Press) except that p-nitrophenyl linked substrates were used instead of methylumbeiliferone linked substrates.

TABLE 2

| Compound | Human GCS (IC$_{50}$ μM) | Human β-glucosidase (IC$_{50}$ μM) | Human α-glucosidase (IC$_{50}$ μM) | Human β-galactosidase (Ki μM) |
|---|---|---|---|---|
| NB-DNJ | 15 | 960 | <20 μM | No inhibition at 1 mM |
| NB-DGJ | Not tested | Not inhibitory | Not inhibitory | 40 |
| Example 2 | 10.6 | Not inhibitory | Not inhibitory | Not inhibitory |
| Example 3 | 4.0 | Not inhibitory | Not inhibitory | Not inhibitory |

Thus, the compounds of the invention exhibit less inhibitory action against both glucosidases and galactosidases (thereby reducing side effects) than compounds such as NB-DNJ or NB-DGJ, while retaining activity against glucosylceramide synthases.

What we claim is:

1. A method for inhibiting glucosylceramide synthase comprising administering to a subject in need thereof an effective amount of the compound (2S,3R,4R,5S)-1-pentyl-2-(hydroxymethyl)-3,4,5-piperidinetriol, in free or pharmaceutically acceptable salt form.

2. The method of claim 1, wherein the subject in need thereof is suffering from Gaucher disease, Sandhoff's disease, Tay-Sachs disease, Fabry disease or GM1 gangliosidosis.

3. The method of claim 2, wherein the subject in need thereof is suffering from Fabry disease.

* * * * *

UNITED STATES PATENT AND TRADEMARK OFFICE
CERTIFICATE OF CORRECTION

| | | |
|---|---|---|
| PATENT NO. | : 8,729,099 B2 | Page 1 of 1 |
| APPLICATION NO. | : 11/196153 | |
| DATED | : May 20, 2014 | |
| INVENTOR(S) | : Butters et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1067 days.

Signed and Sealed this
Twenty-fifth Day of August, 2015

Michelle K. Lee
*Director of the United States Patent and Trademark Office*